US008691761B2

(12) United States Patent
Rivier et al.

(10) Patent No.: US 8,691,761 B2
(45) Date of Patent: *Apr. 8, 2014

(54) SOMATOSTATIN RECEPTOR 2 ANTAGONISTS

(76) Inventors: Jean E. F. Rivier, La Jolla, CA (US);
Judit Erchegyi, San Diego, CA (US);
Jean Claude Reubi, Switzerland (CH);
Helmut R. Maecke, Basel (CH)

( * ) Notice: Subject to any disclaimer, the term of this patent is extended or adjusted under 35 U.S.C. 154(b) by 982 days.

This patent is subject to a terminal disclaimer.

(21) Appl. No.: 12/104,318

(22) Filed: Apr. 16, 2008

(65) Prior Publication Data

US 2008/0299040 A1 Dec. 4, 2008

Related U.S. Application Data

(63) Continuation-in-part of application No. PCT/US2007/081430, filed on Oct. 15, 2007, and a continuation-in-part of application No. 11/872,367, filed on Oct. 15, 2007, now Pat. No. 7,960,342.

(60) Provisional application No. 60/829,637, filed on Oct. 16, 2006.

(51) Int. Cl.
*A61K 38/31* (2006.01)
*A61P 3/10* (2006.01)

(52) U.S. Cl.
USPC .......................................................... 514/7.1

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 3,904,594 | A | 9/1975 | Guillemin et al. |
| 4,372,884 | A | 2/1983 | Brown et al. |
| 4,428,942 | A | 1/1984 | Rivier et al. |
| 5,590,656 | A | 1/1997 | ODorisio et al. |
| 5,776,894 | A * | 7/1998 | Albert et al. ............ 514/11 |
| 5,837,218 | A | 11/1998 | Peers et al. |
| 5,846,934 | A * | 12/1998 | Bass et al. ............ 514/11 |
| 5,874,227 | A | 2/1999 | Rivier |
| 5,925,618 | A | 7/1999 | Baumbach et al. |
| 5,976,496 | A * | 11/1999 | Dean et al. ............ 424/1.69 |
| 6,022,523 | A | 2/2000 | DeGrado et al. |
| 6,262,229 | B1 | 7/2001 | Coy et al. |
| 6,579,967 | B1 | 6/2003 | Rivier et al. |
| 7,019,109 | B2 | 3/2006 | Rivier et al. |
| 2002/0137676 | A1 | 9/2002 | Hsiang et al. |
| 2004/0242842 | A1 | 12/2004 | Maecke et al. |
| 2005/0070470 | A1 | 3/2005 | Coy et al. |
| 2005/0245438 | A1 | 11/2005 | Rivier et al. |
| 2006/0089299 | A1 | 4/2006 | Hsiang et al. |

FOREIGN PATENT DOCUMENTS

| | | |
|---|---|---|
| EP | 0 203 031 | 11/1986 |
| WO | WO-95/22341 | 1/1900 |
| WO | WO-97/11962 | 4/1997 |
| WO | WO-98/24807 | 6/1998 |
| WO | WO-00/12111 | 3/2000 |
| WO | WO-01/44273 | 6/2001 |
| WO | WO-02/32932 | 4/2002 |
| WO | WO-02/072602 | 9/2002 |
| WO | WO-2004/082722 | 9/2004 |
| WO | WO-2008/048942 | 4/2008 |

OTHER PUBLICATIONS

Bossis, et al, "Identification of the Somatostatin Receptor Subtypes Involved in Regulation of Growth Hormone Secretion in Chickens," Molecular and Cellular Endocrinology 182 (2001) 203-213.*
International Search Report (PCT/US2009/040672) dated May 11, 2010.
Antunes, et al., "Are Radiogallium-Labelled DOTA-Conjugated Somatostatin Analogues Superior to those Labelled with Other Radiometals?" Eur. J. Nucl. Med. Mol. Imaging, 2007, Epub ahead of print.
Bass, et al., "Identification and Characterization of Novel Somatostatin Antagonists," Mol. Pharmacol, vol. 50, 1996, pp. 709-715.
Cescato, et al., "Internalization of sst2, sst3, and sst5 Receptors: Effects of Somatostatin Agonists and Antagonists," J. Nucl. Med., vol. 47, 2006, pp. 502-511.
Chen, et al., "Pegylated Arg-Gly-Asp Peptide: 64Cu Labeling and PET Imaging of Brain Tumor Alphavbeta3-integrin Expression," J. Nucl. Med., vol. 45, 2004, pp. 1776-1783.
Ginj,et al,"Radiolabeled Somatostatin Receptor Antagonists are Preferable to Agonists for in Vivo Peptide Receptor Targeting of Tumors," Proceedings of the National Academy of Sciences of the United States of America,vol. 103,No. 44,Oct. 2006.
Gu, et al., "Coupling Specificity Between Somatostatin Receptor sst2A and G Proteins: Isolation of the Receptor-G Protein Complex with a Receptor Antibody," Mol. Endocrinol, vol. 11, 1997, pp. 527-537.
Hirst, et al., "Structure-Activity Studies with Somatostatin: The Role of Tryptophan in Position 8," Regulatory Peptides, vol. 1, 1980, pp. 97-113.
Hocart, et al., "Highly Potent Cyclic Disulfide Antagonists of Somatostatin," J. Med. Chem, vol. 42, 1999, pp. 1863-1871.
Jiang, et al., "GnRH Antagonists: A New Generation of Long Acting Analogues Incorporating Urea Functions at Positions 5 and 6," J. Med. Chem, vol. 44, No. 3, 2001, pp. 453-467.
Jiang, et al., "Orthogonally Protected N-Methyl-Substituted a-Aminoglycines," Prot. Pep. Lett., vol. 3, 1996, pp. 219-224.

(Continued)

*Primary Examiner* — Thomas Heard
(74) *Attorney, Agent, or Firm* — Ramin Amirsehhi

(57) ABSTRACT

The invention is directed to somatostatin analogs which are receptor antagonists of the somatostatin receptor, including receptor-selective antagonists, especially sst2-selective antagonists. Related compounds and compositions are included, including antagonists complexed with or conjugated to radioactive nuclides. The antagonists of the invention are useful in diagnosing and treating neoplastic and non-neoplastic mammalian diseases; such methods, and kits, are encompassed.

10 Claims, 3 Drawing Sheets

(56) References Cited

OTHER PUBLICATIONS

Kaiser, et al., "Color Test for Detection of Free Terminal Amino Groups in the Solid-Phase Synthesis of Peptides," Anal. Biochem, vol. 34, 1970, pp. 595-59.

Kaljuste, et al., "New Method for the Synthesis of N-Methyl Amino Acides Containing Peptides by Reductive Methylation of Amino Groups on the Solid Phase," Int. J. Pept. Prot. Res., vol. 42, 1993, pp. 118-124.

Lloyd, et al., "Activation of Somatostatin Receptor Subtype 2 Inhibits Acid Secretion in Rats," American Journal of Physiology: Gastrointestinal and Liver Physiology, American Physiological Society, vol. 268, No. 1, Pt. 1, 1995, pp. G102-G106.

Magrys, et al., "The Role of Anti-Alpha-Enolase Autoantibodies in Pathogenicity of Autoimmunie-Mediated Retinoopathy," J. Clin. Immunol. vol. 27, 2007, pp. 181-192.

Meyers, et al., "Highly Active Position Eight Analogues of Somatostatin and Separation of Peptide Diastereomers by Partition Chromatography," Biochemistry, vol. 17, 1978, pp. 2326-2330.

Michel, et al., "The Nef Protein of Human Immunodeficiency Virus is a Broad-Spectrum Modulator of Chemokine Receptor Cell Surface Levels that Acts Independently of Classical Motifs for Receptor Endocytosis and Galphai Signaling," Mol. Biol. Cell., vol. 17, 2006, pp. 3578-3590.

Miller, et al., "Analysis of Synthetic Peptides by Capillary Zone Electrophoresis in Organic/Aqueous Buffers," J. Pept. Res, vol. 51, 1998, pp. 444-451.

Miller, et al., "Peptide Chemistry: Development of High-Performance Liquid Chromatography and Capillary Zone Electrophoresis," Biopolymers Pept. Sci., vol. 40, 1996, pp. 265-317.

Miller, et al., "Peptide Chemistry: Development of High-Performance Liquid Chromatography.\ and Capillary Zone Electrophoresis," Biopolymers Pept. Sci., vol. 40, 1996, pp. 265-317.

Murphy, et al., "Octapeptide Analogs of Somatostatin Exhibiting Greatly Enhanced in Vito and in Vitro Inhibition of Growth Hormone Secretion in the Rat," Biochemical and Biophysical Research Communications, Academic Press, San Diego, CA, vol. 132, No. 3, Nov. 15, 1985.

Rajeswaran, et al., "Highly Potent and Subtype Selecive Ligands Derived by N-Methyl Scan of a Somatostatin Antagonist," J. Med. Chem, vol. 44, 2001, pp. 1305-1311.

Raynor, et al., Molecular Pharmacology, vol. 44, 1993, pp. 385-392.

Raynor, et al., Molecular Pharmacology, vol. 43, 1993, pp. 838-844.

Reubi, "Evidence for Two Somatostatin-14 Receptor Types in Rat Brain Cortex," Neurosci. Lett., vol. 49, 1984, pp. 259-26.

Reubi, "In vitro Identification of Vasoactive Intestinal IPeptide Receptors in Human Tumors: Implications for Tumor Imaging," J. Nucl. Med., vol. 36, 1995, pp. 1846-1853.

Reubi, et al., "Concomitant Expression of Several Peptide Receptors in Neuroendocrine Tumours: Molecular Basis for in Vivo Multireceptor Tumour Targeting," European Journal of Nuclear Medicine and Molecular Imaging, vol. 30, No. 5, 2003, pp. 781-793.

Schottelius, et al., "First 18F-Labeled Tracer Suitable for Routine Clinical Imaging of sst Receptor-Expressing Tumors Using Positron Emission Tomography," Clinical Cncer Research, vol. 10, 2004, pp. 3593-3606.

Stewart, et al.,, "Solid Phase Peptide Synthesis," Solid Phase Peptide Synthesis, 2nd Ed., Pierce Chemical Co.: Rockford, IL, 1984, p. 17A.

Sypniewski, et al., "(R)-tert-Butoxycarbonylamino-fluorenylmethoxycarbonyl-glycine from (S)-Benzyloxycarbonyl-serine or fromPapain Resolution of the Corresponding Amide or Methyl Ester," J. Org. Chem., vol. 65, 2000, pp. 6595-6600.

Yabe, et al., "Synthesis and Biological Activity of Somatostating Analogues Modified at the Tryptoophan Residue," Chem. Pharm. Bull, vol. 26, No. 3, 1978.

Hoeger et al., "Preparative Reversed Phase High Performance Liquid Chromatography: Effects of Buffer pH on the Purification of Synthetic Peptides," Biochromatography, 1987, vol. 2, No. 3, pp. 134-142.

Reubi et al., "Detection of Somatostatin Receptors in Surgical and Percutaneous Needle Biopsy Samples of Carcinoids and Islet Cell Carcinomas," Cancer Research, Sep. 1990, vol. 50, pp. 5969-5977.

US Notice of Allowance on 069815-0701 DTD Feb. 3, 2011.

Yang, Lihu et al., "Synthesis and Biological Activities of Potent Peptidomimetics Selective for Somatostatin Receptor Subtype 2," PNAS USA, vol. 95, Sep. 1998, pp. 10836-10841.

Cescato, R., et al., "Design and in Vitro Characterization of Highly sst2-selective somatostatin antagonists suitable for radiotargeting," Journal of Medicinal Chemistry, American Chemical Society, vol. 51, No. 13, Jul. 10, 2008, pp. 4030-4037.

Extended European Search Report received for European Appln. No. 11173287.1 dated Sep. 30, 2011.

Examiners Report received for Australian Appln. No. 2007311137 dated May 22, 2012.

Extended European Search Report for EP 11194516.8—dated Feb. 29, 2012.

Ginj Mihaela et al: "Radiolabeled somatostatin receptor antagonists are preferable to agonists for in vivo peptide receptor targeting of tumors", Proceedings of the National Academy of Sciences of the United States of America, vol. 103, No. 44, Oct. 2006, pp. 16436-16441, XP-002472516.

Lloyd K C K et al: "Activation of somatostatin receptor subtype 2 inhibits acid secretion in rats", American Journal of Physiology: Gastrointestinal and Liver Physiology, American Physiological Society, US, vol. 268, No. 1, pt 1, 1995, pp. G102-G106, XP009097685.

Notification of First Office Action received in Chinese Appln. No. 200780038652.2 mailed Apr. 9, 2012.

Christy Rani R. Grace et al., Ring Size in Octreotide Amide Modulates Differently Agonist versus Antagonist Binding Affinity and Selectivity; J. Med. Chem. 2008, 51, 2676-2681.

* cited by examiner

SOMATOSTATIN RECEPTOR 2 ANTAGONISTS

CROSS-REFERENCE TO RELATED PATENT APPLICATIONS

This application is a continuation-in-part of U.S. application Ser. No. 11/872,367, filed Oct. 15, 2007, and PCT/US2007/081430, filed Oct. 15, 2007, both of which claim the benefit of U.S. Provisional Patent Application Ser. No. 60/829,637 filed Oct. 16, 2006, the contents of each of which are entirely incorporated herein by reference.

GOVERNMENT SUPPORT

This invention was made with Government support under Grant No. DK-59953 awarded by the National Institutes of Health. The Government may have certain rights in this invention.

BACKGROUND OF THE INVENTION

The cyclic tetradecapeptide somatostatin-14 (SRIF) was originally isolated from the hypothalamus and characterized as a physiological inhibitor of growth hormone (GH) release from the anterior pituitary. This tetradecapeptide has a bridging or cyclizing bond between the sulfhydryl groups of the two cysteinyl amino acid residues in the 3- and 14-positions. SRIF and SRIF-related analogs affect multiple cellular processes, specifically those related to GH release, and also inhibit the growth of certain tumors. The analog [D-Trp$^8$]-SRIF, for example, has the amino acid sequence: (cyclo 3-14) H-Ala-Gly-Cys-Lys-Asn-Phe-Phe-D-Trp-Lys-Thr-Phe-Thr-Ser-Cys-OH, and has a much greater potency to inhibit release of GH than SRIF.

SRIF induces its biological effects by interacting with a family of membrane-bound, structurally-similar receptors. Five SRIF receptors have been cloned and are referred to as SSTR 1-5. All five receptors bind SRIF and the 28 amino acid SRIF peptide, SRIF-28 (from porcine gastro-intestinal tract and porcine and ovine hypothalamus), with high affinity. Agonists and antagonists for the various SSTR's have been identified.

Somatostatin peptides and analogs can be modified to allow for selective binding of individual SSTRs. Such peptides and analogs are useful, for example, in differentiating the individual signaling functions of the individual receptors. The use of receptor-specific peptides and analogs have led to the notion that different receptor subtypes mediate distinct functions of SRIF in the body.

Agonists selective for SSTR2 and SSTR5, for example, have been identified and used to reveal distinct functions of these receptors. These two receptors are believed to be the predominant subtypes in peripheral tissues. SSTR2 is believed to mediate the inhibition of growth hormone, glucagon and gastric acid secretion. Octreotide, an agonist, shows some specificity for SSTR2. SSTR5, by contrast, appears to be primarily involved in the control of insulin and amylase release. Analogs have been described that have specificity for SSTR2 and SSTR5, respectively.

SSTR3 mediates inhibition of gastric smooth muscle contraction. Somatostatin analogs that bind specifically to SSTR3 are known.

SSTR4 is found in the pituitary, lungs, GI tract, kidneys and certain tumors to the substantial exclusion of the other SRIF receptors. It is believed to be activated upon binding by SRIF. SSTR4- and SSTR1-specific ligands have been used, for example, in methods for treating endothelial cells. Receptor-selective somatostatin peptide analogs that are specific to SSTR4 are known in the art.

Somatostatin receptors are expressed in pathological states, particularly in neuroendocrine tumors of the gastrointestinal tract. Most human tumors originating from the somatostatin target tissue have conserved somatostatin receptors. The effect of somatostatin signaling was first observed in growth hormone-producing adenomas and TSH-producing adenomas; about one-half of endocrine inactive adenomas display somatostatin receptors. Ninety percent of the carcinoids and a majority of islet cell carcinomas, including their metastasis, usually have a high density of somatostatin receptors. Only 10 percent of colorectal carcinomas and none of the exocrine pancreatic carcinomas contain somatostatin receptors, however. The somatostatin receptors in tumors can be identified, for example, using in vitro binding methods or using in vivo imaging techniques; the latter allow the precise localization of the tumors and their metastasis in the patients. Because somatostatin receptors in gastroenteropancreatic tumors are functional, their identification can be used to assess the therapeutic efficacy of an analog to inhibit excessive hormone release in the patients.

In light of their use as diagnostic and therapeutic targets, there is a need for somatostatin peptide antagonists that bind strongly to SSTR2, while at the same time showing only minimal propensity for binding to the other four receptors. For use as diagnostic imaging agents, such antagonists would have an advantage over SSTR2-selective agonists in that the antagonists would preferably not be internalized.

SUMMARY OF THE INVENTION

This invention is directed to peptides related to somatostatin, i.e., somatostatin peptide analogs, to methods for imaging tumors, and to methods for pharmaceutical treatment of mammals using such peptides. More specifically, the invention relates to shortened receptor-selective somatostatin peptide antagonists, wherein the antagonists include amino acid substitutions and/or additions that confer receptor-selectivity. These peptides are useful in, for example, pharmaceutical compositions. The peptides can be complexed with or conjugated to radioactive nuclides, thereby allowing for methods for diagnosing and treating neoplastic and non-neoplastic mammalian diseases. Peptides that are coupled to chelators or otherwise labeled are also useful for such methods as well as for methods of screening for more effective drugs using such peptides.

In some embodiments, the invention is drawn to a somatostatin antagonist that binds to SSTR2. In some embodiments, the antagonist selectively binds to SSTR2 over the other SSTRs. In other embodiments, however, the antagonist also binds to at least one other SSTR.

In related embodiments, the somatostatin antagonist is not significantly internalized into cells expressing SSTR2, and reduces octreotide-induced internalization of SSTR2.

In further related embodiments, the somatostatin antagonist is a cyclic somatostatin (SRIF) peptide antagonist comprising the amino acid sequence (cyclo 3-14) $Xaa_1$-$Xaa_2$-D-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$, wherein $Xaa_1$ is des-Xaa; $Xaa_2$ is Trp(A), Phe(B), Nal or Tyr, wherein A is H, Cl, F, Br, Me, $NO_2$, OMe or N-formyl and B is H, halogen, $CH_3$, $NO_2$ or $OCH_3$; D-$Xaa_3$ is D-Cys, D-Pen, D-HCys or another D-isomer α-amino acid having an SH-side chain; $Xaa_4$, $Xaa_5$ and $Xaa_6$ are des-Xaa; $Xaa_7$ is Aph($Q_1$), Tyr, ITyr, Ala(thienyl) or Trp(A) where $Q_1$ is Cbm, OH-Cbm, $CH_3$-Cbm, $OCH_3$-Cbm, OEt-Cbm, Cbm-Et(OEt)$_2$ or Hor; Xaa$_8$ is D-Trp(A), Trp(A), Tyr, D-Tyr, Phe(B), D-Phe(B), L or D-BzlHis, L or D-(DNP) His, L or D-Aph(Cbm); Xaa$_9$ is Lys, N$^\alpha$MeLys, hLys, N$^\alpha$MehLys, Orn or N$^\alpha$MeOrn; Xaa$_{10}$ is Thr, Ser or Val; Xaa$_{11}$, Xaa$_{12}$ and Xaa$_{13}$ are des-Xaa; Xaa$_{14}$ is Cys, Pen, hCys or another L-isomer amino acid having an SH side chain; and Xaa$_{15}$ is 2Nal, D-2Nal, Aph(Q$_2$), D-Aph(Q$_2$), (R$_1$)Cha, (R$_1$)D-Cha, (R$_1$)Leu, (R$_1$)D-Leu, Tyr, D-Tyr, Trp, D-Trp or des-Xaa; wherein R$_1$ is H or C$^\alpha$Me, and Q$_2$ is Cbm, OH-Cbm, CH$_3$-Cbm, OCH$_3$-Cbm or OEt-Cbm. "c[Cys- . . . -Cys]" indicates that the peptide is cyclized via cysteine-cysteine linkages.

In further embodiments, the invention includes a compound selected from the group consisting of those set forth in Table 2, which are translated below:

(i) Ac-pNO$_2$Phe-c[DCys-Tyr-DTrp-Lys-Thr-Cys]-DTyr-NH$_2$;
(ii) DOTA-pNO$_2$Phe-c[DCys-Tyr-DTrp-Lys-Thr-Cys]-DTyr-NH$_2$;
(iii) DOTA-pNO$_2$Phe-c[DCys-Tyr-DAph(Cbm)-Lys-Thr-Cys]-DTyr-NH$_2$;
(iv) H$_2$N-pNO$_2$Phe-c[DCys-Tyr-DAph(Cbm)-Lys-Thr-Cys]-2Nal-NH$_2$;
(v) DOTA-pNO$_2$Phe-c[DCys-Tyr-DAph(Cbm)-Lys-Thr-Cys]-2Nal-NH$_2$;
(vi) H$_2$N-pNO$_2$Phe-c[DCys-Aph(Hor)-DAph(Cbm)-Lys-Thr-Cys]-2Nal-NH$_2$;
(vii) H$_2$N-Cpa-c[DCys-Tyr-DTrp-Lys-Thr-Cys]-2Nal-NH$_2$;
(viii) H$_2$N-Cpa-c[DCys-Tyr-DTrp-NMeLys-Thr-Cys]-2Nal-NH$_2$;
(ix) H$_2$N-Cpa-c[DCys-L-Agl(NMe.benzoyl)-DTrp-Lys-Thr-Cys]-2Nal-NH$_2$;
(x) H$_2$N-Cpa-c[DCys-D-Agl(NMe.benzoyl)-DTrp-Lys-Thr-Cys]-2Nal-NH$_2$;
(xi) H$_2$N-Cpa-c[DCys-Leu-DTrp-Lys-Thr-Cys]-2Nal-NH$_2$;
(xii) H$_2$N-Cpa-c[DCys-Aph(Cbm)-DTrp-Lys-Thr-Cys]-2Nal-NH$_2$;
(xiii) Cbm-Cpa-c[DCys-Aph(Cbm)-DTrp-Lys-Thr-Cys]-2Nal-NH$_2$;
(xiv) DOTA-Cpa-c[DCys-Aph(Cbm)-DTrp-Lys-Thr-Cys]-2Nal-NH$_2$;
(xv) DOTA-βAla-Cpa-c[DCys-Aph(Cbm)-DTrp-Lys-Thr-Cys]-2Nal-NH$_2$;
(xvi) DOTA-Peg-Cpa-c[DCys-Aph(Cbm)-DTrp-Lys-Thr-Cys]-2Nal-NH$_2$;
(xvii) H$_2$N-Cpa-c[DCys-Aph(Cbm)-DTrp-Lys-Thr-Cys]-NH$_2$;
(xviii) H$_2$N-Cpa-c[DCys-Aph(Cbm)-DTrp-Lys-Thr-Cys]-Cha-NH$_2$;
(xix) H$_2$N-Cpa-c[DCys-Aph(Cbm)-DTrp-Lys-Thr-Cys]-Aph(Hor)-NH$_2$;
(xx) H$_2$N-Cpa-c[DCys-Aph(Cbm)-DTrp-Lys-Thr-Cys]-DAph(Cbm)-NH$_2$;
(xxi) H$_2$N-Cpa-c[DCys-Aph(Cbm)-DTrp-Lys-Thr-Cys]-Aph(Cbm)-NH$_2$;
(xxii) H$_2$N-Cpa-c[DCys-Aph(Cbm)-DTrp-Lys-Thr-Cys]-DAph(Cbm)-GlyOH;
(xxiii) H$_2$N-Cpa-c[DCys-Aph(CONH—OCH$_3$)-DTrp-Lys-Thr-Cys]-2Nal-NH$_2$;
(xxiv) H$_2$N-Cpa-c[DCys-Aph(CONH—OH)-DTrp-Lys-Thr-Cys]-2Nal-NH$_2$;
(xxv) H$_2$N-Cpa-c[DCys-Aph(Cbm)-5F-DTrp-Lys-Thr-Cys]-2Nal-NH$_2$;
(xxvi) H$_2$N-Cpa-c[DCys-Aph(Cbm)-5F-Trp-Lys-Thr-Cys]-2Nal-NH$_2$;
(xxvii) H$_2$N-Cpa-c[DCys-Tyr-DAph(Cbm)-Lys-Thr-Cys]-2Nal-NH$_2$;
(xxviii) DOTA-Cpa-c[DCys-Tyr-DAph(Cbm)-Lys-Thr-Cys]-2Nal-NH$_2$;
(xxix) H$_2$N-Cpa-c[DCys-Aph(Hor)-DAph(Cbm)-Lys-Thr-Cys]-2Nal-NH$_2$;
(xxx) DOTA-Cpa-c[DCys-Aph(Hor)-DAph(Cbm)-Lys-Thr-Cys]-2Nal-NH$_2$;
(xxxi) DOTA-Cpa-c[DCys-Aph(Hor)-DAph(Cbm)-Lys-Thr-Cys]-DTyr-NH$_2$;
(xxxii) DOTA-pNO$_2$Phe-c[DCys-ITyr-DTrp-Lys-Thr-Cys]-DTyr-NH$_2$; and
(xxxiii) DOTA-Cpa-c[D-Cys-4Aph(Hor)-D-4Aph(Cbm)-Lys-Thr-Cys]-NH$_2$.

Compounds of the invention include SSTR2 somatostatin antagonists, preferably sst2-selective antagonists. Related embodiments include modifications and compositions comprising compounds, and methods of use.

The invention also includes useful compositions comprising the above somatostatin antagonists; such as antagonists which further comprise a chelator, a complexing agent, a conjugating agent or a label; and pharmaceutical composition comprising a somatostatin antagonist and at least one pharmaceutically acceptable excipient.

In some embodiments, the somatostatin antagonist is preferentially taken up by tumors relative to other tissue. For example, in related embodiments, the ratio of antagonist uptake in tumor cells to antagonist uptake in kidney cells is at least about 2.0.

The invention includes methods. Somatostatin antagonists that have selective uptake into tumors are useful in radioimaging and treating tumors. Accordingly, in some embodiments, the invention encompasses a method of radioimaging cancer by administering a somatostatin antagonist coupled to a radionuclide, which permits radioimaging. For methods of treatment, the invention encompasses administration of a therapeutically-effective amount of a composition comprising a somatostatin antagonist and a radionuclide; wherein the composition is administered in an amount sufficient for tumor radiotherapy.

The invention includes kits for diagnostic radioimaging or radiotherapy of cancer. A kit comprises a somatostatin antagonist in a suitable container, and instructions for use. The somatostatin antagonist may come labeled with at least one radionuclide; come unlabeled and provided with at least one radionuclide in a suitable container for labeling; or be unlabeled and capable of being subsequently labeled with at least one radionuclide.

DETAILED DESCRIPTION

Figure 1:
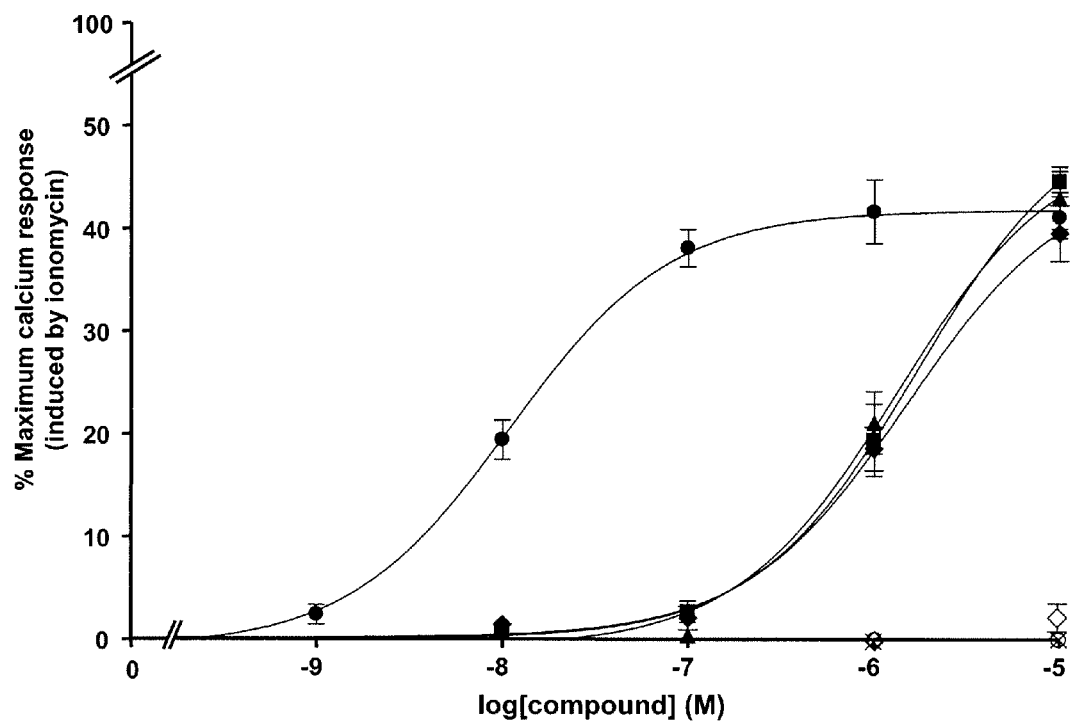
FIG. 1 illustrates the antagonistic properties of some of the sst$_2$ antagonists using the calcium release assay.

As used herein "a" or "an" means one or more, unless specifically indicated to mean only one.

"Administration" as used herein encompasses all suitable means of providing a substance to a patient. Common routes include oral, sublingual, transmucosal, transdermal, rectal, vaginal, subcutaneous, intramuscular, intravenous, intra-arterial, intrathecal, via catheter, via implant etc. In some embodiments, a composition is administered near or directly to the tumor, such as by direct injection into the tumor or injection into the blood such as when the tumor is a tumor of the blood.

"Patient" as used herein includes any vertebrate animal, including equine, ovine, caprine, bovine, porcine, avian, canine, feline and primate species. In one embodiment, the patient is human. A person of ordinary skill in the art will recognize that particular immune co-stimulatory molecules, signaling molecules, cell markers, cell types, infectious agents etc., discussed with reference to one species, may have corresponding analogues in different species, and that such analogues, and their use in corresponding and related species, are encompassed by the present invention.

"Tumor" as used herein includes solid and non solid tumors; and different stages of tumor development from precancerous lesions and benign tumors, to cancerous, malignant and metastatic tumors.

As used herein, such as in the context of SSTR2 antagonists, "uptake" refers to the amount of antagonist found associated with a tumor; and is distinguished from "internalization" which refers to actions at the level of individual cells, such as the ability of a molecule to enter into the intracellular environment. Thus, various embodiments of the invention have high uptake but are not internalized.

As used herein, all temperatures are ° C., and all ratios are by volume. Percentages of liquid materials are also by volume.

The term "selectively binds" or "selective binding" herein refers to the preferential binding of an antagonist to a particular binding partner, e.g., an antagonist that selectively binds SSTR2 binds SSTR2 strongly, while exhibiting weak or no binding to the other SSTRs. Typically, a "selective" antagonist binds 100 times more strongly to the selective receptor than it does to other receptors.

The present invention is related to the unexpected discovery that particular modifications are effective to create peptide analogs of SRIF that are selective for SSTR2 in contrast to the other cloned SRIF receptors. A class of somatostatin peptide analogs has been discovered that are highly SSTR2 selective. These peptide analogs are antagonists of somatostatin, and, although not internalized in cells having SSTR2 receptors, these analogs are taken up in greater quantities than comparable receptor-selective somatostatin peptide agonists. These peptides bind selectively to cloned SSTR2 without activating the receptor, and these peptide analogs, when iodinated or otherwise radiolabeled, retain their desirable biological properties. Thus, these novel peptides are useful for determining the tissue location and cellular expression of the receptor SSTR2, as well as for regulating certain pharmacological functions without certain accompanying side effects heretofore characteristic of administering SRIF. These SRIF peptide antagonists, when radiolabeled, can be used, for example, in scintigraphy to locate tumors expressing these receptors, either in vitro or in vivo, using SPECT or PET. Labels other than radiolabels are known in the art, e.g., fluorescent labels, and can alternatively be used. Where the peptides analogs of the invention include an appropriate chelated radionuclide, these analogs can serve as radiopharmaceuticals that are suitable for radionuclide therapy in treatment of tumors.

SRIF peptide antagonists are provided having a selective affinity for the SRIF receptor SSTR2; they preferably also have a high affinity for SSTR2, e.g., equal to a $K_D$ of about 10 nm or less. These peptides encompass shortened cyclic analogs of SRIF, where the ring portion is shortened to only 6 residues, and where there is one residue at the N-terminus and preferably a residue is also added at the C-terminus. In other words, the 1-, 4-, 5-, 6-, 11-, 12- and 13-position residues are deleted from the 14-residue native SRIF, creating various heptapeptides. These heptapeptides can have a residue, e.g., residue 15, added at the C-terminus to form an octapeptide.

The standard 3-letter abbreviations identify the alpha-amino acid residues, and where the amino acid residue has isomeric forms, it is the L-form of the amino acid that is represented unless otherwise expressly indicated (e.g., Ser=L-serine). "L" or "D" refer to either of the D- and L-isomers of a particular amino acid. Where reference is hereinafter made to a position in the peptide, numbering is made in reference to the corresponding position of the native 14-residue somatostatin (SRIF) peptide.

Examples of representative peptide antagonists exhibiting the desired specificity for SSTR2 include, for example, antagonists where the residues at positions 1, 4-6 and 11-13 are preferably eliminated. Examples include (cyclo 3-14) $Xaa_1$-$Xaa_2$-D-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$; where $Xaa_1$ is des-Xaa; $Xaa_2$ is Trp(A), Phe(B), Nal or Tyr (where A is H, Cl, F, Br, Me, $NO_2$, OMe or N-formyl and B is H, halogen, $CH_3$, $NO_2$ or $OCH_3$); D-$Xaa_3$ is D-Cys, D-Pen, D-HCys or another D-isomer α-amino acid having an SH-side chain; $Xaa_4$, $Xaa_5$ and $Xaa_6$ are des-Xaa; $Xaa_7$ is Aph($Q_1$), Ala(thienyl), Tyr, ITyr or Trp(A) (where $Q_1$ is Cbm, OH-Cbm, $CH_3$-Cbm, $OCH_3$-Cbm, OEt-Cbm, Cbm-Et(OEt)$_2$ or Hor); $Xaa_8$ is D-Trp(A), Trp(A), Tyr, D-Tyr, Phe(B), D-Phe(B), L or D-Bzl-His, L or D-(DNP)His, L or D-Aph(Cbm); $Xaa_9$ is Lys, $N^\alpha$MeLys, hLys, $N^\alpha$MehLys, Orn or $N^+$MeOrn; $Xaa_{10}$ is Thr, Ser or Val; $Xaa_{11}$, $Xaa_{12}$ and $Xaa_{13}$ are des-Xaa; $Xaa_{14}$ is Cys, Pen, hCys or another L-isomer α-amino acid having an SH side chain; and $Xaa_{15}$ is 2Nal, D-2Nal, Aph($Q_2$), D-Aph($Q_2$), ($R_1$)Cha, ($R_1$)D-Cha, ($R_1$)Leu, ($R_1$)D-Leu, Tyr, D-Tyr, Trp, D-Trp or des-Xaa (where $R_1$ is H or $C^\alpha$Me, and $Q_2$ is Cbm, OH-Cbm, $CH_3$-Cbm, $OCH_3$-Cbm or OEt-Cbm). Additionally, the Tyr in the 2-position can be radioiodinated, complexed, conjugated or chelated to an agent attached directly or via a linker to the α-amino group of the N-terminal residue of the peptide analogs. The agents can function, for example, to link a radioactive nuclide, i.e., radionuclide, to the peptide. For example, a macrocyclic chelator, such as, for example, DOTA, can be added at the N-terminus either by joining it directly to $Xaa_2$ or indirectly thereto using a linker such as GABA (gamma amino butyric acid, see e.g., U.S. Pat. No. 6,022,523, the contents of which are incorporated herein by reference in their entirety) or βAla.

Another example of a SRIF analog comprises the amino acid sequence (cyclo 3-14) $Xaa_1$-$Xaa_2$-D-$Xaa_3$-$Xaa_4$-$Xaa_5$-$Xaa_6$-$Xaa_7$-$Xaa_8$-Lys-Thr-$Xaa_{11}$-$Xaa_{12}$-$Xaa_{13}$-Cys; where $Xaa_2$ is substituted Phe; D-$Xaa_3$ is D-Cys; $Xaa_7$ is Aph($Q_1$), Tyr or ITyr; and $Xaa_8$ is D-Trp or D-Aph(Cbm); and where the remaining Xaa groups are as described herein.

As used herein, "Trp" and "D-Trp" refer to the unsubstituted residue as well as a residue where a single substitution for hydrogen is made in either the 5- or 6-position on Trp. The substituents at these position can include, for example, chloro, fluoro, bromo, methyl, nitro and methoxy, with chloro, fluoro and bromo, or with formyl substituting the hydrogen of the indole N.

As used herein, "Nal" refers to an isomer of alanine that is substituted by naphthyl on the β-carbon atom, with the attachment to naphthalene preferably being to the 2-position on the ring, or optionally to the 1-position.

As used herein, "Aph" refers to aminophenylalanine, where the amino group is preferably attached to the 4-position on the phenyl ring, but attachment at either the 2- or 3-position is generally equivalent. As used herein, "Aph (Cbm)" refers to 4-ureido-phenylalanine. By Aph(OH-Cbm) is meant 4-(3-hydroxy)-ureido-phenylalanine. As used herein, "Aph (CH$_3$-Cbm)" refers to 4-(3-methyl)-ureido-phenylalanine. As used herein, "Aph(OCH$_3$-Cbm)" refers to 4-(3-methoxy)-ureido-phenylalanine. As used herein, "Aph [(EtO)$_2$Et-Cbm]" refers to 4-{3-[2-(2-ethoxy-ethoxy)-ethyl]}-ureido-phenylalanine. As used herein, "ITyr" refers to iodinated L-tyrosine. As used herein, "Cpa" refers to chloro-Phe, e.g., 4-ClPhe. As used herein, "Aph(Hor)" refers to 4-[(2,6-dioxo-hexahydro-pyrimidine-4-carbonyl)-amino]-phenylalanine. As used herein, "SRIF" refers to the 14-residue cyclic somatostatin peptide. As used herein, "Cha" refers to cyclohexylalanine. As used herein, "Pen" refers to penicillamine (β-mercapto valine). As used herein, "hLys" or "hCys" refer to the α-amino acid with one additional CH$_2$ group in the side chain.

The C-terminus is usually amidated, although an equivalent, e.g., Gly-OH, can be used. The N-terminus of the peptide can be modified in various ways without significantly, adversely affecting the binding affinity. All of the modifications to these cyclic peptides are considered to be included as a part of the peptides of the overall invention. A variety of additions may be made, for example, to the N-terminal amino acid in the form of a complexing or conjugating agent (Z) that can then be used to join a desired moiety to the peptide or to provide labeling. Such a moiety Z generally can be selected from the group consisting of DOTA- and DTPA-based chelators, NOTA-based chelators, carbonyl compounds, 2-hydrazino nicotinamide (HYNIC), N$_4$-chelators, desferrioxamin, and N$_x$S$_y$-chelators, all optionally complexed with a radioisotope, Tyrosine (Tyr) for halogenation, a fluorescent dye or biotin. Cpa can also serve as a precursor for tritiation. A chelator, such as, for example, DTPA, DOTA, HYNIC and P$_2$S$_2$—COOH can be attached. Chelators include, for example, p-NH$_2$-Bz-DOTA(2-p-aminobenzyl-1,4,7,10-tetraazacyclododecane-1,4,7,10-tetraacetic acid), and DOTA-p-NH$_2$-anilide [1,4,7,10-tetraazacyclododecane-1,4,7,10-tetraacetic acid mono(p-aminoanilide)]. Alternatively, a chelating agent can be covalently linked to the N-terminus via a suitable linker (L) if desired. Suitable linkers include, for example, tyrosine, lysine, diaminobutyric acid, diaminopropionic acid, polyethylene glycol, fatty acids and their derivatives, β-alanine, 5-amino valeric acid, sarcosine, and glucerronic acid. Where Tyr appears at the N-terminus, it can be radioiodinated or otherwise labeled. Acyl groups having not more than about 20 amino acids can also be present at the N-terminus, as the N-terminal residue can also be acylated, if desired, with a bulky moiety without loss of selectivity.

Selectivity for binding of the analog peptides of the invention to SSTR2 has been demonstrated by testing their interaction with the five different cloned human SRIF receptors. Generally, recombinant cells expressing the receptor are washed and homogenized to prepare a crude protein homogenate in a suitable buffer. In a typical assay, an amount of protein from the cell homogenate is placed into a small volume of an appropriate assay buffer at an appropriate pH. Candidate substances, such as potential SRIF agonists and antagonists, are added to the admixture in convenient concentrations, and the interaction between the candidate substance and the receptor polypeptide is monitored. Receptor antagonists that bind to SSTR2 but also show affinity for other receptors may be useful in various compositions and methods of the invention, including kits, and compositions and methods for tumor imaging and treatment. In preferred embodiments, the peptides of the invention bind substantially strongly only to SSTR2, and their binding exhibits high affinity.

Receptor binding assays are performed on cloned SRIF receptors, and competitive assays are used to generate IC$_{50}$ values that are indicative of the concentration of a competitive ligand necessary to displace a saturation concentration of a target ligand being measured from 50% of binding sites.

The invention is also directed to, for example, a method of intraoperatively detecting malignant tumors in the body of a human being in tissues that in healthy condition do not contain substantial quantities of SSTR2. The method includes, for example (i) administering to such being a composition comprising, in a quantity sufficient for detection by a gamma detecting probe, an SSTR2-selective peptide, wherein the peptide is labeled, e.g., radioactively with $^{99m}$Tc, $^{161}$Tb, $^{90}$Y, $^{177}$Lu, $^{123}$I or $^{125}$I, and (ii) after allowing the active substance to be bound and taken up in the tumors and after blood clearance of radioactivity, and subjecting such being to a radiodetection technique in the relevant area of the body by using a gamma-detecting probe.

In one embodiment, the SRIF antagonists of the present invention are highly selective for SSTR2, and they are taken up in greater quantities than earlier SRIF peptide agonists that were only partially specific to SSTR2. More importantly, SRIF antagonists are considered to be useful in treating tumor cells that express SSTR2. Such treatment can include, for example, radiotherapy, the success of which is directly dependent upon the amount of radiation taken up by a tumor. The antagonists of the present invention, as they are taken up and not necessarily internalized by a tumor cell, are, therefore, more effective than known agonists for radiotherapy of tumors.

The antagonists of the present invention are also useful in scintigraphy to determine the distribution of cells and tissues expressing SSTR2 throughout the body. The use of external imaging by radioactive scanning or by magnetic resonance allows semiquantitative detection within the body.

The antagonists of the present invention are also useful for selectively blocking certain of the pharmacological effects that are mediated by SSTR2. The many effects of SRIF are known or will be known in the art.

Radiolabeled antagonists are useful for the therapeutic treatment of malignant tumors in the body of a human being in tissues that, in healthy condition, do not contain substantial quantities of SSTR2. Radiolabeled SSTR2-selective peptide antagonists can be administered in a composition that includes a quantity effective for scintigraphy or for combating or controlling tumors. The radiolabeled peptides can be labeled, for example, with $^{186}$Re, $^{188}$Re, $^{111}$In, $^{113m}$In, $^{71}$As, $^{90}$Y, $^{67}$Cu, $^{99m}$Tc, $^{169}$Er, $^{121}$Sn, $^{127}$Te, $^{142}$Pr, $^{143}$Pr, $^{66}$Ga, $^{67}$Ga, $^{68}$Ga, $^{72}$Ga, $^{127}$Te, $^{195}$Pt, $^{211}$At, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{114}$Ag, $^{124}$I or $^{131}$I.

Labeled SRIF analogs of the invention are useful in drug-screening assays to screen for new effective peptide and non-peptide agents that will bind with high affinity to SSTR2 and are highly effective antagonists. Using a ligand of the invention that is selective for the receptor SSTR2, one can obtain a baseline activity for a recombinantly-produced receptor. A competitive binding assay for SSTR2 with the labeled ligand and the candidate can then be carried out to determine the relative binding affinity. Alternatively, prospective candidates for inhibitors or modifiers, e.g., antagonists of the receptor function, can be directly incorporated into an assay mixture to determine the effect of such candidate on the receptor. By comparing the extent of receptor activity in the presence or absence of the candidate substance, one can then obtain information regarding the effect of the candidate substance on the normal function of the receptor and thus determine its function as either an agonist or an antagonist compared to a known SSTR2-selective analog. The cyclic SRIF peptides described in the following Examples are antagonists, and they can be employed to mediate the normal function of SSTR2.

The peptides of the present invention can be synthesized by classical solution synthesis, but the amidated peptides are preferably synthesized by solid-phase technique, as on a methylbenzhydrylamine (MBHA) resin or a BHA resin, as is known in this art. Peptides having a free carboxyl C-terminus can be synthesized as taught in U.S. Pat. No. 7,019,109, the contents of which are herein incorporated by reference in their entirety. Peptides having an amidated C-terminus can be synthesized as taught in U.S. Pat. No. 5,874,227, the contents of which are herein incorporated by reference in their entirety. Solid-phase synthesis is conducted in a manner that adds amino acids in the chain beginning at the C-terminus in a stepwise manner. Side-chain protecting groups, which are known in the art, are included as a part of any amino acid that has a particularly reactive side chain, and optionally can be used in the case of others such as Trp, where such amino acids are coupled onto the chain being built upon the resin. Such synthesis provides a fully protected intermediate peptidoresin. Protecting groups are generally split off and the peptide is cleaved from the resin support before oxidizing to create a disulfide bond between the Cys side chains.

The SRIF analogs of the present invention are also useful for therapeutic indications, such as modulators of somatostatin. In this use, analogs of the invention are generally effective at levels of less than 100 micrograms per kilogram of body weight. For prolonged action, it can be desirable to use dosage levels of about 0.1 to about 2.5 milligrams per kilogram of body weight. These analogs are soluble in water and thus can be prepared as relatively concentrated solutions for administration.

The peptides of the invention not only provide more selective ligands for binding SSTR2, but the use of labeled peptides, for example, a radiolabeled version of Peptide No. 28, facilitates drug screening for even more effective antagonists.

Screening assays, as are well known in the art, can employ the receptor polypeptide SSTR2 directly from the recombinant host, and can be used to identify agents useful in blocking or mimicking certain aspects of somatostatin as desired while eliminating the undesirable aspects of the hormone that may arise from activation or blocking of other receptors. In this respect, if a radioiodinated analog is desired for screening purposes, Tyr can be added at the N-terminus instead of DOTA, or Tyr can be used in the 2-position instead of Cpa, or a suitable radioligand can be attached by a DOTA chelator. Competitive binding assays with candidate compounds might first be carried out in this manner with SSTR2 to search for high binding affinity; then by screening the multiple SRIF receptors, it could be confirmed whether there was selective binding to only this receptor, as is desired. Non-radiolabeled peptides of the invention may be used to treat diseases of all organs known to express SSTR2, including the lung, gastrointestinal tract and kidneys.

Because additions to the N-terminus of the SRIF analog do not appear to adversely affect the selective binding, it should be clear that these compounds can be complexed with a radioactive nuclide for the purpose of carrying that agent to a tumor or other tissue for which apoptosis is desired. For example, suitable chelating agents, such as DOTA or DTPA or others, can be used to complex the SRIF analog with a highly radioactive metal as indicated hereinbefore. Some examples of suitable chelating groups for chelating a radioactive metal atom are tetradentate chelating agents or groups derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclo-tetradecane-N,N',N'',N'''-tetra-acetic acid (TETA), substituted DTPA, substituted EDTA. Other chelators, as well as radioactive agents, are disclosed in WO 95/22341 and WO 04/082722 and in U.S. Patent Publications 2004/0242842 and 2005/0070470, the disclosures of which are incorporated herein by reference. Preferred chelators are derived from EDTA and DOTA. Some suitable salts are $^{111}$In-oxine, $^{99m}$Tc-tartrate, which can generally be formed in a simple manner under conditions that are not detrimental to the peptide antagonist.

If desired, the solubility of the SRIF antagonists can be improved by acylation of the N-terminal amino group using a hydrophilic compound, such as hydroorotic acid (Hor) or the like, or by reaction with a suitable isocyanate, such as methylisocyanate or isopropylisocyanate, to create a urea moiety at the N-terminus. Other agents can also be N-terminally linked that will increase the duration of action of the SRIF antagonist as known in this art.

These SRIF antagonists or nontoxic salts thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. Such a pharmaceutical composition designed to be used for detecting malignant human tumors, including the metastasis thereof, in tissues may include, in addition to a pharmaceutically acceptable carrier material, and an optional pharmaceutically acceptable adjuvant, the labeled peptide antagonist as the active substance, in a quantity sufficient for external imaging, for detection by a gamma-detecting probe or for combating or controlling tumors. The peptide antagonists should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician to combat specific tumors and cancers or to mediate other conditions where the SSTR2 receptors exert a control function, such as coupling to a tyrosine phosphatase so that stimulation of this enzyme can be carried out to mediate the anti-proliferative effects of SRIF. The required dosage will vary with the particular condition being treated, with the severity of the condition and with the duration of desired treatment.

It has recently been determined that tumors often express several types of peptide receptors (Reubi, J. C.; Waser, B. Concomitant expression of several peptide receptors in neuroendocrine tumours: molecular basis for in vivo multireceptor tumour targeting. *Eur. J. Nucl. Med. Molec. Imaging* 2003, 30, 781-793.). Such groups of multiple peptide receptors may include sst2 receptors, as well as bombesin receptors, CCK receptors, VIP receptors, GLP-1 receptors, neurotensin receptors, secretin receptors, neuromedin B receptors and CRF receptors, etc. In such an instance, the administration of SSTR2 antagonists, in combination as a cocktail, with one or more radiolabeled antagonists to these various receptors should very substantially improve the in vivo targeting of such tumors.

Such peptide antagonists are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like.

It may also be desirable to deliver these SRIF antagonists over prolonged periods of time, for example, for periods of one week to one year from a single administration, and slow release, depot or implant dosage forms may be utilized as well known in this art. For example, a dosage form may contain a pharmaceutically acceptable non-toxic salt of the compound that has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain an SRIF antagonist or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptide antagonists should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of an SRIF antagonist that, when administered peripherally, e.g. intravenously, in a physiologically acceptable composition, is sufficient to achieve a plasma concentration thereof from about 0.1 µg/ml to about 100 µg/ml, preferably from about 1 µg/ml to about 50 µg/ml, more preferably at least about 2 µg/ml and usually 5 to 10 µg/ml. In these amounts, they may be used to desirably affect gastric secretion.

When the composition is to be used for imaging or therapeutic treatments, poor shelf life of the radiolabelled compound and/or the short half-life of the radionuclide may require that the user carry out the labeling reaction with the radionuclide in the clinical hospital or laboratory. In such instances, the various reaction ingredients may be provided to the user in the form of a so-called "kit". The manipulations necessary to perform the desired reaction should be as simple as possible to enable the user to prepare the radioactive labeled composition from the kit using facilities that normally be at one's disposal. Accordingly, a kit for preparing a radiopharmaceutical composition, for detecting and localizing malignant tumors and their metastases in tissues might comprise (i) an SSTR2 selective peptide, an inert pharmaceutically acceptable carrier and/or formulating agent with optional adjuvants, (ii) a solution of a salt or chelate of a radioactive metal isotope, and (iii) instructions for use with a prescription for reacting the ingredients present in the kit.

Preferably, a peptide antagonist to be used as an ingredient of such a kit has been derivatized by a reaction with a chelating agent as defined hereinbefore. The resulting peptide conjugate provides a facility for firmly attaching the radionuclide in a simple manner. Suitable chelating agents for modifying the peptide are described in detail hereinbefore. N-containing di- or polyacetic acids or their derivatives, such as the compounds mentioned before, have proved to be pre-eminently suitable for attaching various metal radionuclides, such as $^{111}$In and $^{113m}$In, to the peptide molecules. The kit to be supplied to the user may also comprise the other ingredients defined above, together with instructions for use, whereas the solution of a salt or chelate of the radionuclide having a limited shelf life, may be supplied to the user separately.

For example, a kit to prepare a radiopharmaceutical composition labeled with $^{99m}$Tc, $^{186}$Re or $^{188}$Re may comprise, in addition to the ingredients defined in (i) and (ii) above, a reducing agent and, if desired, a chelator, and (iii) instructions for use, with a prescription for reacting the ingredients of the kit with $^{99m}$Tc in the form of a pertechnetate solution, or with $^{186}$Re or $^{188}$Re in the form of a perrhenate solution. If desired, various ingredients of the kit may be combined, provided they are compatible. The kit should comprise a reducing agent to reduce the pertechnetate or perrhenate, for example, a dithionite, a metallic reducing agent or a complex-stabilizing reducing agent, e.g. $SnCl_2$, Sn(II)-tartrate, Sn(II)-phosphonate or -pyro-phosphate, or Sn(II)-glucoheptonate. The pertechnetate or perrhenate solution can simply be obtained from a suitable vendor. When the radionuclide is present in the kit itself, the complex-forming reaction with the peptide can simply be produced by combining the components in a neutral medium and causing them to react. For that purpose the radionuclide may be reacted with the peptide in the form of a chelate bound to a comparatively weak chelator, as described hereinbefore.

When the kit comprises a derivatized peptide as defined hereinbefore and is intended for the preparation of a radiopharmaceutical composition, labeled with $^{99m}$Tc, $^{186}$Re or $^{188}$Re, the radionuclide will preferably be added separately in the form of a pertechnetate or perrhenate solution. In that case the kit will comprise a suitable reducing agent and, if desired, a chelator, the former to reduce the pertechnetate or the perrhenate. As a reducing agent may be used, for example, a dithionite or a metallic reducing agent. The ingredients may optionally be combined, provided they are compatible. Such a monocomponent kit, in which the combined ingredients are preferably lyophilized, is excellently suitable for being reacted, by the user, with the radionuclide solution. A metallic reducing agent, for example, Sn(II), Ce(III), Fe(II), Cu(I), Ti(III) or Sb(III); Sn(II), may be used. The peptide constituent of the above-mentioned kits may be supplied as a solution, for example, in the form of a physiological saline solution, or in some buffer solution, but it is preferably present in a dry condition, for example, in the lyophilized condition. When used as a component for an injection liquid it should be sterile, in which, when the constituent is in the dry state, the user should preferably use a sterile physiological saline solution as a solvent. If desired, the above-mentioned constituent may be stabilized in the conventional manner with suitable stabilizers, for example, ascorbic acid, gentisic acid or salts of these acids.

Although the invention has been described with regard to its preferred embodiments, which constitute the best mode presently known to the inventors, it should be understood that various changes and modifications as would be obvious to one having the ordinary skill in this art may be made without departing from the scope of the invention that is set forth in the claims appended hereto. Although the claims variously define the invention in terms of a peptide sequence, it should be understood that such is intended to include nontoxic salts thereof that are well known to be the full equivalent thereof and that are most frequently administered.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The disclosures of all patents and published patent applications set forth hereinbefore are expressly incorporated herein by reference.

EXAMPLES

The following Examples illustrate the provision of a number of SRIF peptide antagonists embodying various features of the invention. In each peptide, the cysteine residues in positions 3 and 14 (numbered according to SRIF) are joined by the cyclizing disulfide bond, and may be annotated as "(cyclo 3-14)" or "c[ ]".

Example 1

The somatostatin analog DOTA-des-AA$^{1,4,5,6,11,12,13}$[Cpa$^2$, D-Cys$^3$, Tyr$^7$, D-4Aph(Cbm)$^8$]-SRIF-2Nal-NH$_2$ having the structure: (cyclo 3-14) DOTA-Cpa-D-Cys-Tyr-D-4Aph(Cbm)-Lys-Thr-Cys-2Nal-NH$_2$ is synthesized. (Peptide 28). Solid phase methodology employing the BOC strategy was used to synthesize the octapeptide in a stepwise manner on an MBHA resin, generally as described in "Example II" of the '277 patent. Boc-D-4Aph(Cbm)-OH was pre-made as described in an earlier publication by Jiang and coupled at position 8.

After cleaving the peptide from the resin and simultaneously removing side chain protecting groups (except Fmoc from Lys) by HF, the peptide was oxidized to create the disulfide bridge in 75% acetic acid solution by adding a 10 percent solution of iodine in methanol until the resultant solution remained orange colored, then stirring for 40 minutes and quenching with ascorbic acid. The crude peptide was purified by preparative RP-HPLC, using a linear gradient 1% B per 1 min increases from the baseline % B (Eluent A=0.1% TFA, eluent B=60% CH$_3$CN, 40% A) at a flow rate of 100 ml/min. DOTA was then coupled at the N-terminus as a chelator by adding DOTA-NHS.3TFA.HPF$_6$ (Macrocyclics, Dallas, Tex.) (198 mg, ~20 μM) in DMF (1 ml) and N,N'-diisopropylethylamine (DIPEA) (36 μl, ~22 μM) to the purified peptide (32 mg, ~20 μM) in dry N,N-dimethylformamide (DMF, 3.5 ml). The mixture was stirred at room temperature overnight. The progress of the reaction was followed by analytical HPLC, and MS analysis showed the desired product, pure DOTA-des-AA$^{1,4,5,6,11,12,13}$[Cpa$^2$, D-Cys$^3$, Tyr$^7$, D-4Aph (Cbm)$^8$, Lys (Fmoc)$^9$]-SRIF-2Nal-NH$_2$, had been obtained. After completion of the reaction, removal of the Fmoc protecting group from the Lys$^9$ side chain was achieved by adding 4 ml of a solution of 20% piperidine in DMF and waiting 30 minutes. DOTA-des-AA$^{1,4,5,6,11,12,13}$[Cpa$^2$, D-Cys$^3$, Tyr$^7$, D-4Aph (Cbm)$^8$]-SRIF-2Nal-NH$_2$ was desalted by preparative RP-HPLC using the same conditions as described above. The purity of the final cyclic DOTA-peptide-conjugate was determined by analytical CZE. It was 94% pure.

MS analysis shows an [M+H]$^+$ mass of 1583.72 Da, which compares very favorably to the calculated mass of 1583.62 Da. The peptide is hereinafter referred to as Peptide No. 28.

Example 2

The initial synthesis described in Example 1 was repeated with two changes; 4Aph (Cbm) and D-Trp were used in the 7- and 8-positions to provide the octapeptide-resin: des-AA$^{1,4,5,6,11,12,13}$[Cpa$^2$, D-Cys$^3$, 4Aph(Cbm)$^7$, D-Trp$^8$, Lys (Fmoc)$^9$]-SRIF-2Nal-MBHA resin.

After cleaving the peptide from the resin as the amide and simultaneously removing the protecting groups from the side chains of the amino acids (except Fmoc from Lys) by HF, the peptide was oxidized to create the disulfide bridge in 75% acetic acid solution by adding a 10 percent solution of iodine in methanol until the resultant solution remained orange colored, then stirring for 40 minutes and quenching with ascorbic acid. The crude peptide was purified by preparative RP-HPLC, using a linear gradient 1% B per 1 min increases from the baseline % B (Eluent A=0.1% TFA, eluent B=60% CH$_3$CN, 40% A) at a flow rate of 100 ml/min. To the purified peptide (34 mg ~24 μM) in dry N,N-dimethylformamide (DMF, 3.5 ml) was added DOTA-NHS.3TFA.HPF$_6$ (Macrocyclics, Dallas, Tex.) (24 mg, 24.2 μM) in DMF (150 μl) and N,N'-diisopropylethylamine (DIPEA) (40 μl, 24 μM). The mixture was stirred at room temperature overnight. The progress of the reaction was followed by analytical HPLC, and after completion of the reaction, 1 ml of piperidine was added to the reaction mixture to remove the Fmoc protecting group from the Lys$^9$ side chain for 30 minutes resulting in DOTA-des-AA$^{1,4,5,6,11,12,13}$[Cpa$^2$, D-Cys$^3$, 4Aph(Cbm)$^7$, D-Trp$^8$]-SRIF-2Nal-NH$_2$, which has the formula: (cyclo 3-14) DOTA-Cpa-D-Cys-4Aph(Cbm)-D-Trp-Lys-Thr-Cys-2Nal-NH$_2$.

This peptide was desalted by preparative RP-HPLC using the same conditions as described above. The purity of the final cyclic DOTA-peptide-conjugate was determined by analytical CZE to be about 98% pure. MS analysis showed an [M+H]$^+$ mass of 1606.50 Da, which compares favorably with the calculated value of 1606.64 Da. It is referred to as Peptide No. 14.

Example 3

The synthesis set forth in Example 1 was repeated omitting 2Nal at the C-terminus and substituting 4Aph(Hor) for Tyr$^7$. Boc-4Aph(Hor)-OH was premade as described in an earlier publication by G. Jiang, J. Stalewski, et al., (2001). "GnRH antagonists: A new generation of long acting analogues incorporating urea functions at positions 5 and 6", *J. Med. Chem.* 44(3): 453-467. Cleavage, deprotection, cyclization and purification of the peptide were carried out as in Example 1. The purified cyclic peptide has the formula: (cyclo 3-14) DOTA-Cpa-D-Cys-4Aph(Hor)-D-4Aph(Cbm)-Lys-Thr-Cys-NH$_2$.

It had a purity on CZE of about 98%. It is referred to as Peptide No. 33. MS analysis showed an [M+H]$^+$ mass of 1525.68 Da, which compares favorably to the calculated value of 1525.58 Da.

Example 4

The synthesis set forth in Example 1 was repeated with one change, instead of pCl-Phe at the N-terminus, pNO$_2$-Phe was used. Cleavage, deprotection, cyclization and purification of the peptide were carried out as in Example 1. The purified cyclic peptide has the formula: (cyclo 3-14) DOTA-pNO$_2$-Phe-D-Cys-Tyr-D-4Aph(Cbm)-Lys-Thr-Cys-2Nal-NH$_2$. It had a purity on CZE of about 98%. It is referred to as Peptide No. 5. MS analysis showed an [M+H]$^+$ mass of 1594.17 Da, which compares favorably to the calculated value of 1594.65 Da.

Example 5

The initial synthesis described in Example 1 was repeated with one change; Aph(Hor) was used instead of Tyr in the 7-position to provide the octapeptide-resin: des-AA$^{1,4,5,6,11,12,13}$[Cpa$^2$, D-Cys$^3$, 4Aph(Hor)$^7$, D-Aph(Cbm)$_8$, Lys (Fmoc)$^9$]-SRIF-2Nal-MBHA resin. Reactions were then carried out as described in Example 2 resulting in DOTA-des-AA$^{1,4,5,6,11,12,13}$[Cpa$^2$, D-Cys$^3$, 4Aph(Hor)$^7$, D-Aph(Cbm)$^8$]-SRIF-2Nal-NH$_2$, which has the formula: (cyclo 3-14) DOTA-Cpa-D-Cys-4Aph(Hor)-D-Aph(Cbm)-Lys-Thr-Cys-2Nal-NH$_2$. (Peptide 30).

The purity of the final cyclic DOTA-peptide-conjugate was determined by analytical CZE to be about 98% pure. MS analysis showed an [M+H]$^+$ mass of 1722.56 Da, which compares favorably to the calculated value of 1722.65 Da.

Example 6

The synthesis set forth in Example 5 was repeated, substituting D-Tyr for 2Nal at the C-terminus. Cleavage, deprotection, cyclization and purification of the peptide were carried out as in Example 1. The purified cyclic peptide has the formula: (cyclo 3-14) DOTA-Cpa-D-Cys-4Aph(Hor)-D-4Aph(Cbm)-Lys-Thr-Cys-D-Tyr-NH$_2$. It had a purity on CZE of about 98%. It is referred to as Peptide No. 31. MS analysis showed an [M+H]$^+$ mass of 1688.83 Da, which compares favorably to the calculated value of 1688.64 Da.

Example 7

The synthesis set forth in Example 4 was repeated substituting D-Tyr for 2Nal at the C-terminus. Cleavage, deprotection, cyclization and purification of the peptide were carried out as in Example 1. The purified cyclic peptide has the formula: (cyclo 3-14) DOTA-pNO$_2$-Phe-D-Cys-Tyr-D-4Aph(Cbm)-Lys-Thr-Cys-D-Tyr-NH$_2$. It had a purity on CZE of about 98%. It is referred to as Peptide No. 3. MS analysis showed an [M+H]$^+$ mass of 1560.63 Da, which compares favorably to the calculated value of 1560.83 Da.

Example 8

The synthesis described in Example 7 was repeated with two changes; ITyr was used at the 7-position and D-Trp was used in the 8-position to provide the octapeptide-resin: des-AA$^{1,4,5,6,11,12,13}$[pNO$_2$-Phe$^2$, D-Cys$^3$, ITyr$^7$, D-Trp$^8$, Lys (Fmoc)$^9$]-SRIF-D-Tyr-MBHA resin.

After cleaving the peptide from the resin as the amide and carrying out reactions as generally described in Example 2, the peptide was obtained having the formula: (cyclo 3-14) DOTA-pNO$_2$-Phe-D-Cys-ITyr-D-Trp-Lys-Thr-Cys-D-Tyr-NH$_2$. (Peptide 32). The purity of the final cyclic DOTA-peptide-conjugate was determined by analytical CZE to be about 98% pure. MS analysis showed an [M+H]$^+$ mass of 1667.74 Da, which compares favorably to the calculated value of 1667.52 Da.

Example 9

In vitro Bioassay: The effects of the various somatostatin analogs were tested in vitro for their ability to bind to isolated cloned receptors expressed on CHO-K1 cells and CCL39 cells. The molecular cloning of the genes encoding multiple somatostatin receptor subtypes permitted the individual expression of these receptors in mammalian cells and the characterization of their respective pharmacological profiles. Five such receptor subtypes, termed SSTR1 through SSTR5, have been cloned and are reported and described in Raynor et al., *Molecular Pharmacology*, 43, 838-844 (1993) and in Raynor et al., *Molecular Pharmacology*, 44, 385-392 (1993). These references describe binding assays that can be used to determine whether particular SRIF analogs bind selectively to one or more of the 5 receptor types and also whether they bind to such receptor types with high or low affinity. Because these receptor types have now generally been characterized with regard to their pharmacological profiles, knowledge of the results of such binding studies, along with knowledge of the unique patterns of distribution of these receptors in the body indicate that each receptor subtype may mediate distinct but overlapping physiological effects of SRIF. As a result, compounds that bind selectively to receptors SSTR2, for example, can be used to modulate a particular physiological function of SRIF without potentially having an undesired effect resulting from another physiological function of SRIF that is mediated by other SRIF receptors.

CHO-K1 cells were grown in Ham's F-12 medium, and CCL39 cells were grown in Dulbecco's modified Eagle's medium/Ham's F-12(1:1) mix, supplemented with 10% fetal bovine serum, 100 U/ml penicillin and 100 μg/ml streptomycin, in humidified air containing 5% CO$_2$ at 37° C. Cells were washed twice with and scraped into ice-cold 0.05 M Tris-HCl (pH 7.4), collected by centrifugation, and homogenized using a rotor/stator/system in the same buffer. After centrifugation at 120 g for 5 min at 4° C., the supernatant was collected and centrifuged again at 48,000 g for 30 min at 4° C. The resulting pellet was resuspended in ice-cold Tris buffer, transferred into a microfuge tube, and centrifuged at 20,000 g for 15 min at 4° C. After withdrawal of the supernatant, the membrane pellet was stored at −80° C.

Receptor autoradiography was performed on 20 μm thick cryostat sections of the membrane pellets, mounted on microscope slides, and then stored at −20° C. For each of the tested compounds, complete displacement experiments were performed with the universal somatostatin ligand radioligand $^{125}$I-[Leu$^8$,D-Trp 22,Tyr$^{25}$]-somatostatin 28 that binds with strong affinity to all five receptors. Increasing concentrations of the unlabeled peptide were used ranging from 0.1-1000 nM. Unlabeled somatostatin-28 was run in parallel using the same increasing concentrations, as a control. IC$_{50}$ values were calculated after quantification of the data using a computer-assisted image processing system as known in this art.

At concentrations of 100 nM, Peptide No. 28 had minimal effects on the binding of the SRIF-28 radioligand to SSTR1, SSTR3, SSTR4 and SSTR5. In contrast, it selectively bound to SSTR2, displacing the binding of the radioligand to human SSTR2 with an IC$_{50}$ value of about 1.8 nM.

The potencies of certain SRIF analogs to inhibit radioligand binding of $^{125}$I-[Leu$^8$,D-Trp$^{22}$,Tyr$^{24}$]SRIF-28 to the various cloned human SRIF receptors are shown in the following Table 1 wherein the IC$_{50}$ values are given in nanomolar concentration. The numbers in parentheses indicate the number of times the particular binding test was carried out.

TABLE 1

| Compound | hSSTR1 | hSSTR2 | hSSTR3 | hSSTR4 | hSSTR5 |
|---|---|---|---|---|---|
| | | IC$_{50}$ (nM) | | | |
| Peptide No. 28 406-034-15 | >1,000 (2) | 1.8 ± 0.2 (3) | >1,000 (2) | >1,000 (2) | >1,000 (2) |
| Peptide No. 14 363-246-15 | >1,000 (3) | 9.4 ± 1.6 (3) | >1,000 (2) | 816 ± 114 (3) | >1,000 (3) |
| Peptide No. 33 363-300-15 | >1,000 (2) | 230; 219 (2) | >1,000 (2) | >1,000 (2) | >1,000 (2) |
| Peptide No. 5 406-032-20 | >1,000 (2) | 1.5 ± 0 (2) | >1,000 (2) | >1,000 (2) | >1,000 (2) |
| Peptide No. 30 363-298-15 | >1,000 (2) | 1.7 ± 0.3 (3) | >1,000 (2) | >1,000 (2) | >1,000 (2) |
| Peptide No. 31 406-094-15 | >1,000 (2) | 0.6 ± 0.05 (2) | >1,000 (2) | >1,000 (2) | >1,000 (2) |
| Peptide No. 3 406-092-15 | >1,000 (2) | 0.53 ± 0.06 (2) | >1,000 (2) | >1,000 (2) | >1,000 (2) |
| Peptide No. 32 406-090-15 | >1,000 (2) | 1.02 ± 0.88 (2) | >1,000 (2) | 493 ± 206 (2) | >1,000 (2) |

Moreover, all the peptides tested and reported in the Table above showed no significant internalization in the cells while antagonizing octreotide-induced internalization. Peptides Nos. 28, 5, 30, 31, 3 and 32 exhibited very good binding properties and excellent tumor targeting properties in vivo, namely huge uptake in the sst2 tumors at 4 h and 24 h, and excellent tumor to kidney ratio; such can be blocked by excess cold peptide.

The following protocol was used to determine biodistribution

HEK-sst$_2$ Cell Implantation in Nude Mice

Animals were kept, treated, and cared for in compliance with the guidelines of the Swiss regulations (approval 789). Athymic female nude mice were implanted subcutaneously with 10 million HEK-sst$_2$ cells freshly suspended in sterile PBS. Ten to fourteen days after inoculation, the mice showed solid palpable tumor masses (tumor weight 60-150 mg) and were used for the in vivo biodistribution experiments.

Confirmation that the transfected tumors were indeed expressing solely sst$_2$ was obtained in resected tumor samples tested in vitro with somatostatin receptor autoradiography using subtype selective ligands.

In Vivo Biodistribution of $^{111}$In-Labeled Antagonists and Agonists

Mice were injected into a tail vein with 10 μmol of $^{111}$In-radiolabeled peptide (approx. 0.15-0.2 MBq) in 0.1 ml NaCl solution (0.9%, with 0.1% BSA). The biodistribution of was studied at 4 h or 24 h after injection. The organs of interest were collected, blotted dry, weighed, their radioactivity measured and the percentage of injected activity per gram (% IA/g) calculated.

In one experiment 5 μCi $^{111}$In-labelled Peptide No. 28 was injected into nude mice bearing HEK-sst2 tumors, 3-4 mice per sample group. The presence of 2000-fold (by mole) of unlabelled compound inhibited binding. The following biodistribution was observed.

| Organ | 4 h | | 4 h blocking | | 24 h | |
|---|---|---|---|---|---|---|
| blood | 0.26 | 0.03 | 0.19 | 0.03 | 0.06 | 0.01 |
| heart | 0.36 | 0.03 | 0.12 | 0.01 | 0.09 | 0.01 |
| liver | 1.52 | 0.03 | 0.88 | 0.10 | 0.52 | 0.08 |
| spleen | 0.62 | 0.06 | 0.36 | 0.10 | 0.28 | 0.05 |
| lung | 2.31 | 1.25 | 0.30 | 0.10 | 0.31 | 0.08 |
| kidney | 7.48 | 0.43 | 6.95 | 0.39 | 4.50 | 0.36 |
| stomach | 20.27 | 2.55 | 1.84 | 0.37 | 3.38 | 0.69 |
| intestine | 1.44 | 1.18 | 0.25 | 0.04 | 0.23 | 0.05 |
| adrenal | 3.17 | 0.69 | 0.21 | 0.01 | 0.77 | 0.14 |
| pancreas | 29.83 | 2.86 | 2.41 | 0.73 | 2.35 | 0.47 |
| pituitary | 8.29 | 3.38 | 0.21 | 0.06 | 1.73 | 0.84 |
| muscle | 0.19 | 0.05 | 0.06 | 0.01 | 0.10 | 0.05 |
| bone | 1.23 | 0.24 | 0.16 | 0.05 | 0.85 | 0.66 |
| sst2 tumor | 28.41 | 2.98 | 2.36 | 0.27 | 21.49 | 0.95 |

| Organ | 4 h | 24 h |
|---|---|---|
| tumor:kidney | 3.8 | 4.8 |
| tumor:pancreas | 0.95 | 9.1 |
| tumor:pituitary | 3.4 | 12.4 |
| tumor:blood | 109.3 | 358 |
| tumor:muscle | 149.5 | 215 |
| tumor:bone | 23.9 | 25.3 |

The following biodistribution was observed when 5 μCi $^{111}$In-labelled Peptide No. 14 was injected into nude mice bearing HEK-sst2 tumors, 3 mice per sample group.

| Organ | 1 h | 4 h | 24 h | 48 h | 72 h |
|---|---|---|---|---|---|
| tumor:kidney | 1.95 | 2.54 | 3.84 | 2.93 | 3.27 |
| tumor:adrenal | 14.12 | 72.27 | 57.80 | 31.71 | 33.53 |
| tumor:pancreas | 2.44 | 43.15 | 162.00 | 157.78 | 150.70 |
| tumor:pituitary | 6.54 | 34.36 | 26.00 | 25.70 | 12.11 |
| tumor:blood | 24.92 | 152.94 | 410.79 | 595.61 | 741.89 |
| tumor:muscle | 67.19 | 279.34 | 347.94 | 275.34 | 266.45 |
| tumor:bone | 13.14 | 48.44 | 50.11 | 26.99 | 36.86 |

A similar experiment, with $^{177}$Lu-labeled Peptide No. 14 (5 μCi into nude mice bearing HEK-sst2 tumors, 3 mice per sample group) gave the following distribution, expressed as the ratio of signal in tumor:organ.

| Organ | 4 h | 24 h |
|---|---|---|
| blood | 0.20 | 0.061 |
| heart | 0.25 | 0.084 |
| liver | 0.80 | 0.399 |
| spleen | 1.03 | 0.232 |
| lung | 2.88 | 0.438 |
| kidney | 10.82 | 6.034 |
| stomach | 17.26 | 1.825 |

-continued

| Organ | 4 h | 24 h |
|---|---|---|
| intestine | 0.96 | 0.282 |
| adrenal | 2.85 | 1.370 |
| pancreas | 26.11 | 1.177 |
| pituitary | 20.18 | 8.637 |
| muscle | 0.22 | 0.153 |
| bone | 1.06 | 0.915 |
| sst2 | 34.90 | 25.650 |

By comparison $^{111}$In-labelled Peptide No. 33 showed the following biodistribution after injecting 5 µCi into nude mice bearing HEK-sst2 and sst3 tumors, 4 mice per sample group. The presence of 1000-fold of unlabelled compound inhibited binding:

| Organ | 4 h | STDEV | 4 h blocking | STDEV | 24 h | STDEV |
|---|---|---|---|---|---|---|
| blood | 0.12 | 0.01 | 0.12 | 0.01 | 0.04 | 0.01 |
| heart | 0.06 | 0.01 | 0.05 | 0 | 0.05 | 0.02 |
| liver | 0.33 | 0.04 | 0.32 | 0.04 | 0.25 | 0.08 |
| spleen | 0.17 | 0.03 | 0.2 | 0.01 | 0.12 | 0.02 |
| lung | 0.27 | 0.06 | 0.21 | 0.04 | 0.18 | 0.1 |
| kidney | 13.74 | 1.26 | 10.3 | 1.75 | 7.07 | 1.12 |
| stomach | 0.16 | 0.02 | 0.12 | 0.01 | 0.12 | 0.03 |
| intestine | 0.11 | 0.02 | 0.09 | 0 | 0.06 | 0.01 |
| adrenal | 0.26 | 0.04 | 0.23 | 0.05 | 0.15 | 0.04 |
| pancreas | 0.06 | 0.01 | 0.05 | 0.01 | 0.04 | 0.01 |
| pituitary | 0.46 | 0.36 | 0.14 | 0.1 | 0.05 | 0.04 |
| muscle | 0.03 | 0.01 | 0.02 | 0.01 | 0.03 | 0.01 |
| bone | 0.09 | 0.06 | 0.04 | 0.03 | 0.06 | 0.01 |
| sst2 | 3.56 | 0.65 | 0.22 | 0.14 | 1.21 | 0.31 |
| sst3 | 0.22 | 0.03 | 0.14 | 0.07 | 0.21 | 0.11 |

The biodistribution relative to the sst2 tumor was as follows:

| Organ | 4 h | 4 h blocking | 24 h |
|---|---|---|---|
| blood | 29.7 | 1.8 | 30.3 |
| kidney | 0.3 | 0.0 | 0.2 |
| pancreas | 59.3 | 4.4 | 30.3 |
| pituitary | 7.7 | 1.6 | 24.2 |
| muscle | 118.7 | 11.0 | 40.3 |
| bone | 39.6 | 5.5 | 20.2 |

$^{111}$In-labelled Peptide No. 5 showed the following biodistribution after injecting 5 µCi into nude mice bearing HEK-sst2 tumors, 3-4 mice per sample group. The presence of 2000-fold of unlabelled compound inhibited binding (not shown).

| Organ | 4 h | 24 h |
|---|---|---|
| tumor:kidney | 4.0 | 5.0 |
| tumor:pancreas | 1.8 | 16.0 |
| tumor:pituitary | 14.3 | 15.3 |
| tumor:blood | 83.9 | 357.7 |
| tumor:muscle | 183.6 | 268.3 |
| tumor:bone | 35.4 | 33.5 |

Peptide No. 30 was studied in greater detail. $^{111}$In-labelled Peptide No. 30 showed the following biodistribution after injecting 5 µCi into nude mice bearing HEK-sst2 tumors, 4 mice per sample group. A 2000 fold excess of cold peptide showed blocking:
Tumor to Organ Ratio for Select Organs.

| Organ | 1 h | 4 h | 4 h block | 24 h | 48 h | 72 h |
|---|---|---|---|---|---|---|
| blood | 19.7 | 112.8 | 75.6 | 519.6 | 657.5 | 307.3 |
| heart | 27.9 | 88.2 | 88.2 | 259.8 | 263.0 | 184.4 |
| liver | 10.2 | 18.3 | 7.6 | 34.6 | 23.1 | 18.8 |
| spleen | 13.2 | 27.1 | 13.2 | 66.6 | 47.0 | 36.9 |
| lung | 2.6 | 18.4 | 22.0 | 61.9 | 69.2 | 46.1 |
| kidney | 2.4 | 3.3 | 0.9 | 4.3 | 3.5 | 3.2 |
| stomach | 1.4 | 2.1 | 18.9 | 7.5 | 4.6 | 5.7 |
| intestine | 7.9 | 25.0 | 44.1 | 81.2 | 54.8 | 61.5 |
| adrenal | 2.5 | 5.5 | 26.5 | 16.8 | 16.0 | 13.2 |
| pancreas | 0.6 | 1.2 | 23.0 | 7.0 | 6.5 | 6.0 |
| pituitary | 2.4 | 2.9 | 8.1 | 5.4 | 10.4 | 9.9 |
| muscle | 41.5 | 165.9 | 132.3 | 288.7 | 263.0 | 92.2 |
| bone | 18.2 | 43.4 | 22.0 | 44.0 | 35.5 | 29.7 |

$^{177}$Lu-labelled Peptide No. 30 showed the following biodistribution after injecting 5 µCi into nude mice bearing HEK-sst2 tumors, 4 mice per sample group:

| Organ | 4 h | 24 h | 72 h |
|---|---|---|---|
| tumor:blood | 95.82 | 2380.57 | 2679.44 |
| tumor:heart | 29.24 | 217.19 | 129.21 |
| tumor:liver | 6.60 | 16.81 | 13.57 |
| tumor:spleen | 15.47 | 21.01 | 20.61 |
| tumor:lung | 5.37 | 94.69 | 29.51 |
| tumor:kidney | 3.04 | 4.83 | 3.13 |
| tumor:stomach | 0.48 | 0.89 | 0.90 |
| tumor:intestine | 7.27 | 20.27 | 6.74 |
| tumor:adrenal | 1.26 | 10.00 | 2.50 |
| tumor:pancreas | 0.39 | 0.62 | 0.84 |
| tumor:pituitary | 1.70 | 9.09 | 4.08 |
| tumor:muscle | 148.53 | 332.56 | 750.80 |
| tumor:bone | 11.04 | 35.08 | 82.58 |

$^{111}$In-labelled Peptide No. 31 showed the following biodistribution after injecting 5 µCi into nude mice bearing HEK-sst2 tumors, 3-4 mice per sample group:

| Organ | 4 h | 24 h |
|---|---|---|
| tumor:kidney | 5.51 | 6.29 |
| tumor:pancreas | 1.48 | 11.33 |
| tumor:pituitary | 3.52 | 6.73 |
| tumor:blood | 122.84 | 537.22 |
| tumor:muscle | 136.11 | 127.01 |
| tumor:bone | 20.94 | 16.28 |

Under the same protocol $^{111}$In-labelled Peptide No. 3 showed the following distribution.

| Organ | 4 h | 24 h |
|---|---|---|
| tumor:kidney | 5.35 | 4.56 |
| tumor:pancreas | 1.91 | 14.69 |
| tumor:pituitary | 5.39 | 4.98 |
| tumor:blood | 222.39 | 283.53 |
| tumor:muscle | 146.02 | 128.61 |
| tumor:bone | 28.41 | 21.30 |

The peptides of the invention not only provide more selective ligands for binding SSTR2, but the use of labeled peptides, for example, a radiolabeled version of Peptide No. 28, facilitates drug screening for even more effective antagonists.

Example 10

Additional experiments, and experiments with additional peptides, are described below.

Starting Materials. MBHA resin with a capacity of 0.3-0.4 mequiv/g was used in the solid phase syntheses. All Boc-$N^\alpha$protected amino acids with side chain protection: Cys (Mob), Lys($\epsilon$-2Cl-Z), Lys(Fmoc), Thr(Bzl), Tyr(2Br-Z) and ITyr(3Br-Bzl) were commercially available (Bachem Inc., Torrance, Calif.; Chem Impex, Wood Dale, Ill.; Reanal, Budapest, Hungary) except Boc-Aph(Cbm)-OH, Boc-DAph(Cbm)-OH, Boc-Aph(Cbm-OCH$_3$)—OH, Boc-Aph(Cbm-OH)—OH, Boc-Aph(Hor)-OH, (Jiang, et al. "GNRH antagonists: A new generation of long acting analogues incorporating urea functions at positions 5 and 6". *J. Med. Chem.* 2001, 44, 453-467 Fmoc-D/L-Agl(NMe,Boc)-OH, (Jiang et al., "Orthogonally protected N-methyl-substituted α-aminoglycines." *Prot. Pep. Lett.* 1996, 3, 219-224.) Fmoc-D-Agl(Boc)-OH, Sypniewski, M et al., "(R)-tert-Butoxycarbonylamino-fluorenylmethoxycarbonyl-glycine from (S)-Benzyloxycarbonyl-serine or from papain resolution of the corresponding amide or methyl ester." *J. Org. Chem.* 2000, 65, 6595-6600.) Boc-5F-Trp-OH, Boc-5F-DTrp-OH which were synthesized in the laboratory. 1,4,7,10-Tetraazacyclododecane-1,4,7,10-tetraacetic acid mono(N-hydroxysuccinimide).ester.3CH$_3$COOH.HPF$_6$ (DOTA-NHS) was purchased from Macrocyclics Inc. (Dallas, Tex., USA). All reagents and solvents were ACS grade and were used without further purification.

Peptide Synthesis. Peptides were synthesized by the solid-phase approach either manually or on a CS-Bio Peptide Synthesizer Model CS536. (Stewart, J. M.; Young, J. D. Solid Phase Peptide Synthesis. *Solid Phase Peptide Synthesis;* 2nd ed.; Pierce Chemical Co.: Rockford, Ill., 1984; pp 17A) 3-equiv excess of Boc-amino acid (1.2 mmol) based on the original substitution of the resin was used for each coupling. Peptide couplings were mediated for 1 h by DIC/HOBt (1.2 mmol/1.8 mmol) in dimethylformamide (DMF) and monitored by the qualitative ninhydrin test. (Kaiser, et al. "Color test for detection of free terminal amino groups in the solid-phase synthesis of peptides." *Anal. Biochem.* 1970, 34, 595-59). Boc removal was achieved with trifluoroacetic acid (TFA) (60% in CH$_2$Cl$_2$, 1-2% ethanedithiol or m-cresol) for 20 min. An isopropyl alcohol (1% m-cresol) wash followed TFA treatment and then successive washes with triethylamine (TEA) solution (10% in CH$_2$Cl$_2$), methanol, triethylamine solution, methanol and CH$_2$Cl$_2$ completed the neutralization sequence. The ureido group (Cbm) at the N-terminus of 13 was introduced on the resin. The N-terminal Boc group of the fully assembled peptide was deprotected with TFA in the usual manner (Jiang et al. "GnRH antagonists: A new generation of long acting analogues incorporating urea functions at positions 5 and 6." *J. Med. Chem.* 2001, 44, 453-467), after neutralization, the carbamoylation proceeded with NaOCN (100 mg, 0.65 mmol) in N-methylpirrolidinone (NMP) (4 mL) and glacial acetic acid 3 mL per gram of initial resin. The mixture was agitated at room temperature for 30 min and ninhydrin test indicated a complete reaction. The completed peptide was then unprotected and cleaved from the resin by HF containing the scavengers anisole (10% v/v) and methyl sulfide (5% v/v) for 60 min at 0° C. The diethyl ether precipitated crude peptides were cyclized in 75% acetic acid (200 mL) by addition of iodine (10% solution in methanol) until the appearance of a stable orange color. Forty minutes later, ascorbic acid was added to quench the excess of iodine.

For the synthesis of 9, we used unresolved Fmoc-D/L-Agl(NMe,Boc)-OH and the two diastereomers were separated readily during the standard HPLC purification steps. (Miller et al. "Peptide chemistry: Development of high-performance liquid chromatography and capillary zone electrophoresis." *Biopolymers Pept. Sci.* 1996, 40, 265-317; Hoeger, et al. "Preparative reversed phase high performance liquid chromatography. II. Effects of buffer pH on the purification of synthetic peptides." *Biochromatography* 1987, 2, 134-142) The optical configuration of the two diastereomers was tentatively inferred from a comparison of the HPLC elution behavior with analogue synthesized separately as diastereomers of known optical configuration. In short: after coupling Fmoc-DAgl(Boc)-OH in position 7, the side chain protecting Boc group was removed with 60% TFA, washed, neutralized and to the 0.9 g peptide resin (0.36 mmol/g) swollen in dichloromethane, Dod-Cl (130 mg; 0.5 mmol) was added along with DIEPA (500 µL). The mixture was shaken for an hour to complete the alkylation. The resin was washed, and shaken after the addition of formaldehyde (2 mL, 37% solution) in NMP (18 mL) and acetic acid (100 µL). After 5 min, sodium cyanoborohydride (300 mg) was added and the mixture was shaken for 60 min. After the removal of the Dod group with TFA (60%) for 30 min, benzoyl chloride (500 µL) was used to acylate the free secondary amino group of the side chain. (Kaljuste, et al. "New method for the synthesis of N-methyl amino acids containing peptides by reductive methylation of amino groups on the solid phase." *Int. J. Pept. Prot. Res.* 1993, 42, 118-124.) Removal of the $N^\square$-Fmoc protecting group with 20% piperidine in NMP in two successive 5 and 15 min treatments was followed by the standard elongation protocol until completion of the peptide. The peptide was cleaved, deprotected and cyclized as described above. On HPLC, this D configuration diastereomer coeluted with the earlier eluting diastereomer from the synthesis performed with the unresolved amino acid, therefore the slower eluting peptide (9) was tentatively identified as the L-Agl(NMe, benzoyl)[7] containing analogue.

Generally, for the synthesis of the DOTA-peptide-conjugates, the side chain of Lys[9] was protected with an Fmoc protecting group that stays on after HF cleavage. To a solution of the RP-HPLC purified [Lys(Fmoc)[9]]sst$_2$-antagonist (~20 µM) in dry DMF (800 µL) was added a solution of DOTA-NHS-ester (38 mg, 48 µM) in DMF (160 µL) and N,N'-Diisopropylethylamine (DIPEA) (40 µL, 24 EM). The mixture was stirred at room temperature for 5 hours. The progress of the reaction was followed by analytical HPLC. After completion of the reaction, a preparative RP-HPLC purification was performed yielding the pure DOTA-[Lys(Fmoc)][9]-sst$_2$-antagonist. Removal of the Fmoc protecting group from the Lys side chain was achieved with 20% piperidine/DMF solution resulting in the DOTA-sst$_2$-antagonist, which was further purified by preparative RP-HPLC.

Purification of Peptides. The crude, lyophilized peptides were purified by preparative RP-HPLC (Miller, et al. "Peptide chemistry: Development of high-performance liquid chromatography and capillary zone electrophoresis." *Biopolymers Pept. Sci.* 1996, 40, 265-317) on a 5 cm×30 cm cartridge, packed in the laboratory with reversed-phase 300 Å Vydac C$_{18}$ silica (15-20 µm particle size). The peptides eluted with a flow rate of 100 mL/min using a linear gradient of 1% B per 3 min increase from the baseline % B (eluent A=0.25 N TEAP pH 2.25, eluent B=60% CH$_3$CN, 40% A). All peptides were subjected to a second purification step carried out with eluents A=0.1% TFA in water and B=60% CH$_3$CN/40% A on the same cartridge using a linear gradient of 1% B per min increase from the baseline % B. Analytical HPLC screening of the purification was performed on a Vydac $C_{18}$ column (0.46×25 cm, 5 µm particle size, 300 Å pore size) connected to a Rheodyne injector, two Waters pumps Model 501, System Controller Programmer, Kratos 750 UV detector, and Houston Instruments D-5000 strip chart recorder. The fractions containing the product were pooled and subjected to lyophilization.

Characterization of SRIF Analogues (Table 2). The purity of the final peptides was determined by analytical RP-HPLC performed with a linear gradient using 0.1 M TEAP pH 2.5 as eluent A and 60% $CH_3CN$/40% A as eluent B on a Hewlett-Packard Series II 1090 Liquid Chromatograph connected to a Vydac $C_{18}$ column (0.21×15 cm, 5 µm particle size, 300 Å pore size), Controller Model 362 and a Think Jet printer. Capillary zone electrophoresis (CZE) analysis was performed as described earlier. (Miller, C. et al. "Analysis of synthetic peptides by capillary zone electrophoresis in organic/aqueous buffers." *J. Pept. Res.* 1998, 51, 444-451) Each peptide was found to have a purity of >95% by HPLC and CZE. Mass spectra (MALDI-MS) were measured on an ABI-Perseptive DE-STR instrument. The instrument employs a nitrogen laser (337 nm) at a repetition rate of 20 Hz. The applied accelerating voltage was 20 kV. Spectra were recorded in delayed extraction mode (300 ns delay). All spectra were recorded in the positive reflector mode. Spectra were sums of 100 laser shots. Matrix α-cyano-4-hydroxycinnamic acid was prepared as saturated solutions in 0.3% trifluoroacetic acid and 50% acetonitrile. The observed monoisotopic $(M+H)^+$ values of each peptide corresponded with the calculated $(M+H)^+$ values.

Reagents. All reagents were of the best grade available and were purchased from common suppliers. [$Tyr^3$]-octreotide (Reubi, J. C. "Evidence for two somatostatin-14 receptor types in rat brain cortex." *Neurosci. Lett.* 1984, 49, 259-26) was from Novartis Inc. (Basel, Switzerland). All other peptides, including Coy-14 (Rajeswaran, et al. "Highly potent and subtype selective ligands derived by N-methyl scan of a somatostatin antagonist." *J. Med. Chem.* 2001, 44, 1305-1311 were synthesized at the Salk Institute. The R2-88 antibody to the $sst_{2A}$ receptor was generated as previously described and has been extensively characterized. (Gu, Y. Z.; Schonbrunn, A. "Coupling specificity between somatostatin receptor sst2A and G proteins: isolation of the receptor-G protein complex with a receptor antibody." *Mol. Endocrinol.* 1997, 11, 527-537). The secondary antibody Alexa Fluor 488 goat anti-rabbit IgG (H+L) was from Molecular Probes, Inc. (Eugene, Oreg.), the monoclonal anti-T7 antibody from Novagen (Madison, Wis.), the goat anti-mouse IgG horseradish peroxidase conjugate from Bio-Rad Laboratories, Inc. (Hercules, Oreg.); the Fluo-4NW Calcium Assay kit was from Molecular Probes, Inc. (Eugene, Oreg.), substrate mix for horseradish peroxidase (ABTS) was from Bio-Rad Laboratories, Inc. (Hercules, Oreg.), lactalbumin hydrolysate was from HyClone (Logan, Utah).

Cell lines. CHO-K1, CCL39 cells stably expressing the cloned five human $sst_s$ and the HEK293 cell line expressing the T7-epitope tagged human $sst_{2A}$ receptor (HEK-$sst_2$) were grown as described herein. All culture reagents were from Gibco BRL, Life Technologies, (Grand Island, N.Y.).

Receptor autoradiography. Cell membrane pellets were prepared as previously described, and stored at −80° C. Receptor autoradiography was performed on 20-µm thick cryostat (Microm HM 500, Walldorf, Germany) sections of the membrane pellets, mounted on microscope slides, and then stored at −20° C. For each of the tested compounds, complete displacement experiments with the universal SRIF radioligand [$Leu^8$, $D$-$Trp^{22}$, $^{125}I$-$Tyr^{25}$]-SRIF-28 ($^{125}I$-[LTT]-SRIF-28) (2,000 Ci/mmol; Anawa, Wangen, Switzerland) using 15,000 cpm/100 µl and increasing concentrations of the unlabelled peptide ranging from 0.1-1000 nM were performed. As control, unlabelled SRIF-28 was run in parallel using the same increasing concentrations. The sections were incubated with $^{125}I$-[LTT]-SRIF-28 for 2 hours at room temperature in 170 mmol/L Tris-HCl buffer (pH 8.2), containing 1% BSA, 40 mg/L bacitracin, and 10 mmol/L $MgCl_2$ to inhibit endogenous proteases. The incubated sections were washed twice for 5 min in cold 170 mmol/L Tris-HCl (pH 8.2) containing 0.25% BSA. After a brief dip in distilled water to remove excess salts, the sections were dried quickly and exposed for 1 week to Kodak BioMax MR film. $IC_{50}$ values were calculated after quantification of the data using a computer-assisted image processing system as described previously. (Reubi, et al., "Detection of somatostatin receptors in surgical and percutaneous needle biopsy samples of carcinoids and islet cell carcinomas." *Cancer Res.* 1990, 50, 5969-5977.) Tissue standards (Autoradiographic [$^{125}I$] microscales, GE Healthcare; Little Chalfont, UK) that contain known amounts of isotope, cross-calibrated to tissue-equivalent ligand concentrations were used for quantification. (Reubi, J. C. "In vitro identification of vasoactive intestinal peptide receptors in human tumors: Implications for tumor imaging." *J. Nucl. Med.* 1995, 36, 1846-1853).

Immunofluorescence-based $sst_2$ Internalization Assay. Immunofluorescence microscopy-based internalization assay for $sst_2$ was performed with HEK-$sst_2$ using the $sst_2$-specific antibody R2-88 as described elsewhere herein. HEK-$sst_2$ cells were treated either with vehicle alone, the $sst_2$ agonist [$Tyr^3$]-octreotide at a concentration of 100 nM, [$Tyr^3$]-octreotide at a concentration of 100 nM in the presence of an excess of the SRIF analogues to be tested (100 times the concentration of [$Tyr^3$]-octreotide), or with the SRIF analogues to be tested alone at a concentration of 10 µM, and then processed for immunofluorescence microscopy as described previously.

Quantitative assay for $sst_2$ internalization (ELISA) Receptor internalization was determined using an ELISA to quantitate T7-epitope-tagged human $sst_2$ on the cell surface. HEK-$sst_2$ cells were seeded on poly-D-lysine (20 µg/mL) coated 24-well plates (250,000 cells per well) in growth medium and cultured for 1 day at 37° C. and 5% $CO_2$. On the day of the assay, cells were incubated with the monoclonal anti-T7 antibody at a dilution of 1:3000 for 2 h at room temperature in DMEM containing 5 g/L lactalbumin hydrolysate+20 mM HEPES, pH 7.4 (DMEM-LH) to label cell surface receptors. After washing with DMEM-LH to remove unbound antibody, cells were incubated for 30 min at 37° C. and 5% $CO_2$ either without or with the ligands added at the concentrations indicated. Incubations were terminated by placing the plates in an ice bath. Cells were then washed twice with cold PBS and fixed for 10 min at room temperature with 3% paraformaldehyde in PBS (pH 7.4). Nonspecific binding sites were blocked by incubating the cells for 60 min at room temperature with PBS containing 1% bovine serum albumin (BSA; Fraction V; SERVA, Heidelberg, Germany). Cells were then incubated for 60 min at room temperature with goat anti-mouse IgG horseradish peroxidase conjugate (1:1000) in PBS containing 1% BSA. After 3 additional washes with PBS, antibody binding was measured by adding 0.3 mL substrate mix for horseradish peroxidase (ABTS). The $OD_{405}$ was measured after an approximately 30 min incubation at room temperature. The amount of $sst_2$ remaining at the cell surface after ligand treatment was calculated as the absorbance measured in treated cells expressed as a percentage of the absorbance in untreated cells. Nonspecific absorbance was determined in experiments in which HEK293-sst2 cells were incubated without the anti-T7 antibody.

Each data point represents the mean ±SEM of three experiments performed in duplicates.

Calcium release assay. Intracellular calcium release was measured in HEK-$sst_2$ using the Fluo-4NW Calcium Assay kit as described previously (Magrys, et al. "The role of anti-alpha-enolase autoantibodies in pathogenicity of autoimmune-mediated retinopathy." *J. Clin. Immunol.* 2007, 27, 181-192; Michel et al. "The Nef protein of human immunodeficiency virus is a broad-spectrum modulator of chemokine receptor cell surface levels that acts independently of classical motifs for receptor endocytosis and Galphai signaling." *Mol. Biol. Cell.* 2006, 17, 3578-3590). In brief, HEK-$sst_2$ cells were seeded (25,000 cells per well) in poly-D-lysine (20 µg/mL) coated 96 well plates and cultured for 1 day at 37° C. and 5% $CO_2$ in culture medium. At the day of the experiment, the cells were washed with assay buffer (1×HBSS, 20 mM HEPES) containing 2.5 mM probenecid, and then loaded with 100 µL/well Fluo-4NW dye in assay buffer containing 2.5 mM probenecid for 30 min at 37° C. and 5% $CO_2$ and then for further 30 min at room temperature. To measure the intracellular calcium mobilization after stimulation with the SRIF analogues to be tested, the dye-loaded cells were transferred to a SpectraMax M2$^e$ (Molecular Devices, Sunnyvale, Calif.). Intracellular calcium mobilization was recorded in a kinetic for 60 sec at room temperature monitoring fluorescence emission at 520 nm (with $\lambda_{ex}$=485 nm) in the presence of the analogues at the concentrations indicated. Maximum fluorescence (Fmax) was measured after the addition of 25 µM ionomycin. Baseline (control) measurements were taken for dye-loaded, untreated cells. Data are shown as percentage of Fmax (% Fmax) as reported previously. (Magrys, et al. *J. Clin. Immunol.* 2007, 27, 181-192; Michel et al. *Mol. Biol. Cell.* 2006, 17, 3578-3590). All experiments were repeated at least three times in triplicate.

Results and Discussion

All of the analogues shown in Table 2 were synthesized either manually or automatically on a MBHA resin using the Boc-strategy, diisopropylcarbodiimide (DIC)/HOBt (1-hydroxybenzotriazole) for amide bond formation and trifluoroacetic acid (TFA) for Boc removal. The peptide resins were treated with hydrogen fluoride (HF) in the presence of scavengers to liberate the fully deprotected crude linear peptides. Cyclization of the cysteines was mediated by iodine in an acidic milieu. Purification was carried out using multiple HPLC steps. DOTA was coupled to the Lys(Fmoc)$^9$ protected analogues in solution. The purity of the peptides was characterized by HPLC, capillary zone electrophoresis and mass spectrometry. Miller, et al. *Biopolymers Pept. Sci.* 1996, 40, 265-317; Miller, et al. "Analysis of synthetic peptides by capillary zone electrophoresis in organic/aqueous buffers." *J. Pept. Res.* 1998, 51, 444-451). The observed monoisotopic mass (M+H)$^+$ values of each peptide correspond to the calculated mass (M) values. Results are shown in Table 2.

To investigate their $sst_s$ binding properties, the peptides were tested for their ability to bind to cryostat sections from membrane pellets of cells expressing the five human $sst_s$ (Table 3). For each of the tested compounds, complete displacement experiments with the universal SRIF radioligand [Leu$^8$,DTrp$^{22}$, $^{125}$I-Tyr$^{25}$]SRIF-28 using increasing concentrations of the unlabelled peptide ranging from 0.1-1000 nM were performed. The unlabelled SRIF-28 was run in parallel using the same increasing concentrations, as a control. Results are shown in Table 3.

Inverting chirality at positions 2 and 3 in the octreotide scaffold (H-DPhe$^2$-c[Cys$^3$-Phe$^7$-DTrp$^8$-Lys$^9$-Thr$^{10}$-Cys$^{14}$]-Thr$^{15}$-ol, SRIF numbering) was reported to be the key structural modification converting a SRIF agonist into an antagonist. Additional substitutions resulted in partially selective antagonists Acetyl-pNO$_2$Phe-c[DCys-Tyr-DTrp-Lys-Thr-Cys]-DTyr-NH$_2$ or H-Cpa-c[DCys-Tyr-DTrp-Lys-Thr-Cys]-2Nal-NH$_2$. These antagonists display preferentially high binding affinity for $sst_2$, and lower or no affinity to $sst_3$, $sst_4$ and $sst_5$. None of the analogues bind to $sst_1$. Using these lead compounds, we have designed SRIF antagonists that were more affine (>3-fold) and more $sst_2$-selective than those reported so far. See, e.g. Bass, et al. "Identification and characterization of novel somatostatin antagonists." *Mol. Pharmacol.* 1996, 50, 709-715; Hocart, et al., "Highly potent cyclic disulfide antagonists of somatostatin." *J. Med. Chem.* 1999, 42, 1863-1871.

Analogues of antagonists like Acetyl-pNO$_2$Phe$^2$-c[DCys$^3$-Tyr$^7$-DTrp$^8$-Lys$^9$-Thr$^{10}$-Cys$^{14}$]-DTyr$^{15}$-NH$_2$ (1) and H-Cpa$^2$-c[DCys$^3$-Tyr$^7$-DTrp$^8$-Lys$^9$-Thr$^{10}$-Cys$^{14}$]-2Nal$^{15}$-NH$_2$ (7) were synthesized to investigate the effect of different substitutions on binding affinity, receptor-subtype selectivity, overall hydrophilicity as well as agonism and antagonism.

The substitution of the N-terminal acetyl group by DOTA in 1 (IC$_{50}$=3.6 nM at $sst_2$) resulted in 2, which bound to $sst_2$ with an IC$_{50}$=1.5 nM suggesting that the DOTA moiety, which is crucial for the radiolabeling with $^{111}$In, $^{90}$Y, or $^{177}$Lu for in vivo targeting, is well tolerated by $sst_2$ (Table 3). This conclusion is confirmed further with several additional examples.

The introduction of DAph(Cbm)$^8$ in place of DTrp$^8$ in 2 yielded 3 (IC$_{50}$=0.75 nM). It is noteworthy that these two substitutions are cumulative thus resulting in the most potent $sst_2$ antagonist in this series, with no measurable binding affinity to any of the other receptors. Further replacement of DTyr$^{15}$ in 3 by 2Nal$^{15}$ yielded 5 with a similar binding affinity for $sst_2$ (IC$_{50}$=1.3 nM). Analogue 4, a peptide with the same sequence as 5 but without DOTA at its N-terminus still had excellent binding affinity for $sst_2$ (IC$_{50}$=2.6 nM) and also bound measurably to $sst_3$ (IC$_{50}$=384 nM). Substitution of Tyr in position 7 by Aph(Hor) resulting in 6 had no effect on $sst_2$ binding affinity and selectivity when compared with the parent 4 (IC$_{50}$=2.6 and 2.7 nM at $sst_2$ and 384 nM and 451 nM at $sst_3$, respectively, and no binding affinity at the other three receptors) (Table 3).

H-Cpa$^2$-c[DCys$^3$-Tyr$^7$-DTrp$^8$-Lys$^9$-Thr$^{10}$-Cys$^{14}$]-2Nal$^{15}$-NH$_2$ (7) published by Hocart et al. ("Highly potent cyclic disulfide antagonists of somatostatin. *J. Med. Chem.* 1999, 42, 1863-1871) was also used as a second lead for $sst_2$-selective antagonists. This antagonist has IC$_{50}$ values in our binding assay equal 5.7, 112 and 218 nM at $sst_{2/3/5}$, respectively, as compared to the reported values of 26, 93 and 48 nM. In the assays 7 is more potent than reported at $sst_2$ by a factor of five and less potent at $sst_5$ by the same factor.

Whereas N$^\alpha$-methylation of Lys$^9$ in 7 to yield 8 increased binding affinity 5-fold in Hocart et al. assay at $sst_2$ (K$_i$=26 nM and 5.51 nM, respectively) with no improvement at $sst_3$ or $sst_5$, (K$_i$=ca. 50-100 nM) our results showing no such improvement at $sst_2$ do not support this observation and, as a result, we did not pursue the use of this substitution in the design of additional $sst_2$-selective analogues. Instead, 9 was synthesized with an L-Agl(NMe,benzoyl)$^7$ in an attempt to constrain the orientation of the side chain at position 7. The use of such aminoglycine derivatives (betides) had been taken advantage of in the design of an $sst_3$-selective antagonist. While 9 lost some binding affinity for $sst_2$ (3-fold) as compared to that of 7, it also lost comparable binding affinity for $sst_3$ and $sst_5$. This observation further suggests that position 7 is critical for all three $sst_{2,3,5}$. In fact, 10 with the D-Agl(NMe, benzoyl)[7] lost binding affinity at $sst_2$ while retaining similar binding affinities as 7 at $sst_{3/4/5}$, thus accomplishing one of our goals of identifying the or those residues/conformations responsible for binding to any particular receptor (i.e., $sst_2$ in this case).

Whereas substituting Phe by Leu at position 7 in 7 yielded 11 that lost 10-fold binding affinity for $sst_2$ and selectivity, substitution by Aph(Cbm) yielded 12 which exhibited similar binding affinity and selectivity as 7 at the five $sst_s$. N-terminal carbamoylation of 12 to yield 13, improved binding affinity slightly at $sst_{3/4}$ with some loss of binding affinity for $sst_2$ as compared to 12. Addition of DOTA to 12 resulted in 14 whose $sst_2$ binding affinity is similar to that of 12 and increased selectivity for $sst_2$. Interestingly, addition of a spacer in 14 between DOTA and the octapeptide such as βAla in 15 and Peg in 16 was unexpectedly detrimental in terms of $sst_2$ binding affinity yet favorable for $sst_3$ and neutral at $sst_{1/4/5}$. (Chen, et al., "Pegylated Arg-Gly-Asp peptide: 64Cu labeling and PET imaging of brain tumor alphavbeta3-integrin expression." *J. Nucl. Med.* 2004, 45, 1776-1783; Antunes, et al. "Are radiogallium-labelled DOTA-conjugated somatostatin analogues superior to those labelled with other radiometals?" *Eur. J. Nucl. Med. Mol. Imaging* 2007, Epub ahead of print.)

From the observation that 2Nal[15] may contribute to the $sst_3$, $sst_4$, and $sst_5$ binding pocket, 17 (missing this residue) was synthesized and found to have similar binding affinities when compared to the parent 12. Substitution of 2Nal[15] in 12 by different other residues such as Cha in 18, Aph(Hor) in 19, DAph(Cbm) in 20 and Aph(Cbm) in 21 did not markedly influence affinity at $sst_2$ or selectivity. This is noteworthy in that there is only a three-fold difference in binding affinity at $sst_2$ for 20 (D-configuration and $IC_{50}$=5.4 nM) and 21 (L-configuration and $IC_{50}$=15 nM) where the C-terminal amino acid is of the D or L configuration, respectively. This supports the earlier observation that DTyr (as in 1 and 2) or 2Nal (as in 4 and 5) are both equally accepted. On the other hand, extension of the sequence of 20 by Glycine-OH as in 22, leads to significant loss of affinity at all receptors.

In order to modulate the overall hydrophilicity of 7 (with Tyr at position 7), the following carbamates (Aph(Cbm)[7]) 12, (Aph(CONH—OCH$_3$)[7]) 23 and (Aph(CONH—OH)[7]) 24 were introduced at position 7. Whereas binding affinities for these analogues are not different from that of the parent 7, the order of elution of these analogues on HPLC at neutral pH suggests that 24 (RT=31.6 min) may be more hydrophilic than 7 (RT=34.8 min), 12 (RT=31.9 min) and 23 (RT=34.2 min). Since hydrophilicity may be a critical criterion for a clinically relevant radioligand, subtle differences in structure may favor one of these analogues when selecting a clinical candidate. The fact that 12, 23 and 24 are not superior to 7 in terms of $sst_2$ binding affinity and selectivity, supports our previous finding that residue 7 is not an essential contributor to the $sst_2$ pharmacophore.

The effect of substitutions at position 8 was then investigated. There is literature precedent suggesting that 5F-Trp is a favorable substitution for Trp[8]. (Meyers, et al. "Highly active position eight analogues of somatostatin and separation of peptide diastereomers by partition chromatography." *Biochemistry* 1978, 17, 2326-2330.) When introduced in 12, to yield 25 and 26, a slight improvement in binding affinity for the three $sst_{2/3/5}$ was observed as expected for the 5F-DTrp-containing 25 and less so for the corresponding L-isomer-containing 26. No increase in selectivity however was seen for either analogue.

It was therefore very rewarding to find out that substitution of DTrp[8] in 7 by DAph(Cbm)[8] yielding 27 was clearly superior in terms of $sst_2$ selectivity with improved binding affinity. Further derivatization with the addition of DOTA at the N-terminus yielded 28 with additional increase in binding affinity to $sst_2$ and greater than 500-fold selectivity at all other receptors.

Substitution of Tyr[7] in 27 and 28 with Aph(Hor) yielded 29 and 30. Whereas 29 retained high binding affinity at $sst_2$ it also exhibited moderate binding affinity for $sst_3$; the binding affinity at $sst_3$ was lost upon the introduction of DOTA (30). Substitution of Tyr[7] in 2 with ITyr yielded 32, the binding affinity of which was similar to that of 2 at $sst_2$.

2Nal[15] in 30 was then substituted by DTyr[15] to yield 31. Of all analogues presented here 31 (because of its hydrophilicity, RT=13.2 min) may be the preferred candidate for bio-distribution and ultimately clinical investigation over 3 (RT=13.6 min), 5 (RT=26.1 min), 28 (RT=26.7 min), 29 (RT=27.7 min) or 32 (RT=25.0 min) that are equally potent and selective in the binding assay. It is remarkable that the dipeptide sequence -Aph(Hor)-DAph(Cbm)- found in 29-31 is identical to that found in degarelix (Fe-200486), a gonadotropin releasing hormone antagonist where it played a critical role in stabilizing a turn and in extending duration of action. (Jiang, et al. *J. Med. Chem.* 2001, 44, 453-467)

Put in perspective, the most affine DOTA-containing antagonists presented here (3 and 31) have binding affinities three to four-fold greater than that of SRIF-28 with no detectable binding affinity at any of the other four $sst_s$ and are therefore potential candidates for clinical use.

All of the analogues tested here are antagonists in the calcium release assay in HEK293 cells stably expressing the human $sst_2$. Testing them alone, they do not affect calcium release up to 10 μM. However, the agonistic effect of the $sst_2$ agonist [Tyr$^3$]-octreotide can be competitively antagonized with a 100-fold excess of each of the analogues applied individually. FIG. 1 illustrates the antagonistic properties of some of the $sst_2$ antagonists using the calcium release assay.

The antagonistic property of the analogues 3, 31 and 32 was also confirmed in an immunofluorescence-based internalization assay (Cescato et al. "Internalization of $sst_2$, $sst_3$, and $sst_5$ Receptors: Effects of Somatostatin Agonists and Antagonists." *J. Nucl. Med.* 2006, 47, 502-511) with HEK293 cells stably expressing the human $sst_2$.

Figure 2:
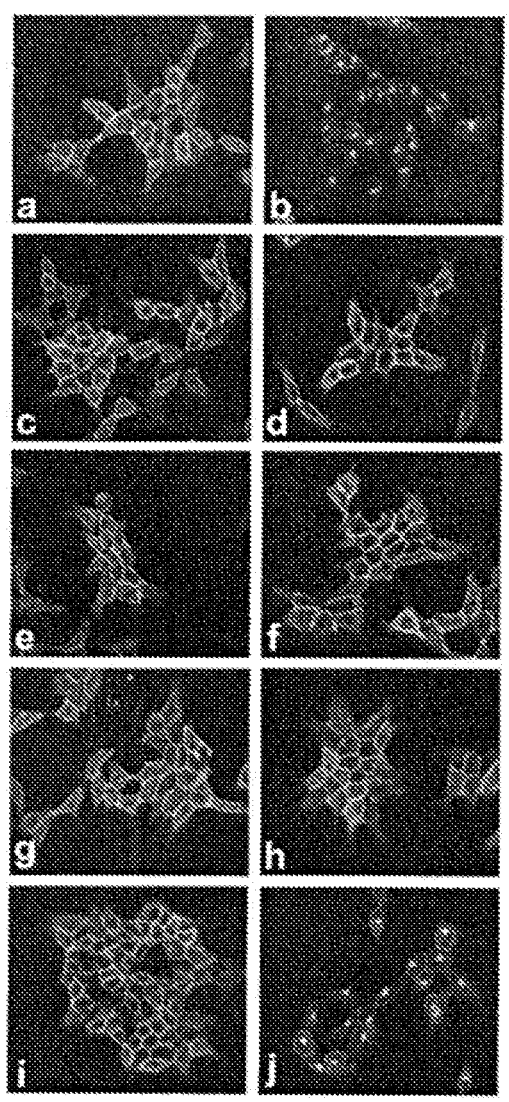
FIG. 2 illustrates that, although the control agonist [Tyr$^3$]-octreotide can induce sst$_2$ internalization, the tested sst$_2$-selective antagonists have no effect when given alone, even at a concentration of 10 μM. Moreover, they prevent sst$_2$ internalization induced by [Tyr$^3$]-octreotide.
Figure 3:
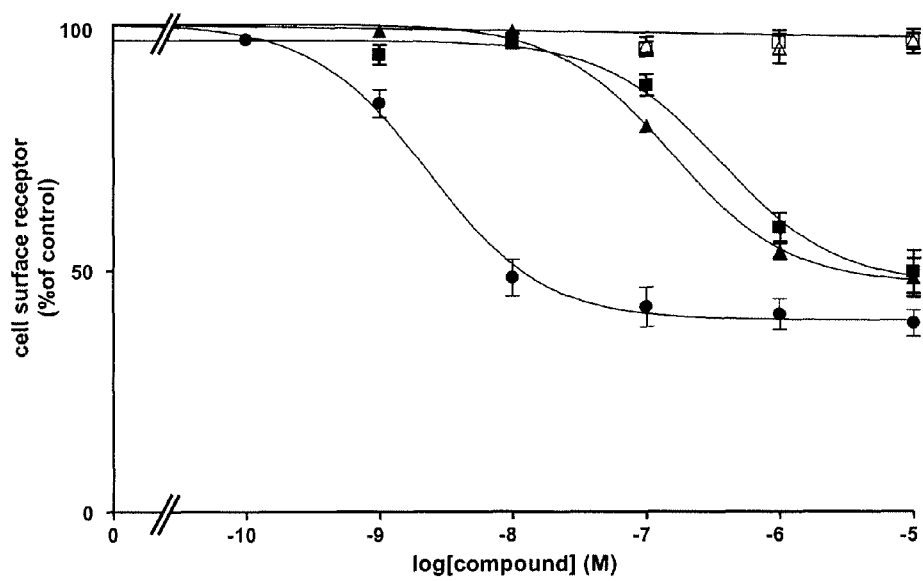
FIG. 3 shows the antagonistic properties of another analogue (32) in the ELISA internalization assay.

FIG. 2 illustrates that, although the control agonist [Tyr$^3$]-octreotide can induce $sst_2$ internalization, the tested $sst_2$-selective antagonists have no effect when given alone, even at a concentration of 10 μM. Moreover, they prevent $sst_2$ internalization induced by [Tyr$^3$]-octreotide. FIG. 3 shows the antagonistic properties of another analogue (32) in the ELISA internalization assay.

To conclude, a great majority of the analogues reported here have a high affinity binding in the nanomolar range for $sst_2$ and often a high selectivity for $sst_2$ as well. Best compounds were 3 and 31 (with $IC_{50}$ values below 1 nM) followed by 32, 5, 28, 2 and 29. All of these antagonists are of particular interest, since they all include a DOTA moiety, making them candidates for in vivo tumor targeting.

Further research into the three dimensional structure (such as via NMR) of sst2 selective antagonists will allow the identification of important structural motifs, with the expectation that similarly structured compounds may function similarly.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention.

Various features of the invention are emphasized in the claims that follow.

TABLE 2

Physico-chemical Properties of $Sst_2$ Antagonists.

Structure of SRIF analogues
Residues are numbered according to SRIF numbering
H-Ala$^1$-Gly$^2$-c[Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$]-OH (SRIF)
Substitution in H-DPhe$^2$-c[Cys$^3$-Phe$^7$- DTrp$^8$-Lys$^9$-Thr$^{10}$-Cys$^{14}$]-Thr$^{15}$-ol (octreotide)

| | N-ter-minus | 2 | 3 | 7 | 8 | 9 | 10 | 14 | 15 | C-ter-minus | Purity HPLC[a] | CZE[b] | MS[c] $M_{calc}$ | M + H$_{obs}$ |
|---|---|---|---|---|---|---|---|---|---|---|---|---|---|---|
| 1 | Ac-[1] | pNO$_2$Phe- | DCys- | Tyr- | DTrp- | Lys- | Thr- | Cys- | DTyr- | NH$_2$ | 99 | 99 | 1196.44 | 1197.59 |
| 2 | DOTA- | pNO$_2$Phe- | DCys- | Tyr- | DTrp- | Lys- | Thr- | Cys- | DTyr- | NH$_2$ | 95 | 97 | 1540.61 | 1541.46 |
| 3 | DOTA- | pNO$_2$Phe- | DCys- | Tyr- | DAph(Cbm)- | Lys- | Thr- | Cys- | DTyr- | NH$_2$ | 99 | 99 | 1559.63 | 1560.83 |
| 4 | H$_2$N— | pNO$_2$Phe- | DCys- | Tyr- | DAph(Cbm)- | Lys- | Thr- | Cys- | 2Nal- | NH$_2$ | 99 | 99 | 1207.47 | 1208.54 |
| 5 | DOTA- | pNO$_2$Phe- | DCys- | Tyr- | DAph(Cbm)- | Lys- | Thr- | Cys- | 2Nal- | NH$_2$ | 99 | 99 | 1593.65 | 1594.17 |
| 6 | H$_2$N— | pNO$_2$Phe- | DCys- | Aph(Hor)- | DAph(Cbm)- | Lys- | Thr- | Cys- | 2Nal- | NH$_2$ | 99 | 99 | 1346.50 | 1347.59 |
| 7 | H$_2$N—[2] | Cpa- | DCys- | Tyr- | DTrp- | Lys- | Thr- | Cys- | 2Nal- | NH$_2$ | 99 | 99 | 1177.43 | 1178.43 |
| 8 | H$_2$N—[3] | Cpa- | DCys- | Tyr- | DTrp- | NMeLys- | Thr- | Cys- | 2Nal- | NH$_2$ | 97 | 99 | 1191.45 | 1192.52 |
| 9 | H$_2$N— | Cpa- | DCys- | L-Agl(NMe, benzoyl) | DTrp- | Lys- | Thr- | Cys- | 2Nal- | NH$_2$ | 95 | 98 | 1204.45 | 1205.51 |
| 10 | H$_2$N— | Cpa- | DCys- | D-Agl(NMe, benzoyl) | DTrp- | Lys- | Thr- | Cys- | 2Nal- | NH$_2$ | 98 | 99 | 1204.45 | 1205.48 |
| 11 | H$_2$N— | Cpa- | DCys- | Leu- | DTrp- | Lys- | Thr- | Cys- | 2Nal- | NH$_2$ | 99 | 99 | 1127.45 | 1128.46 |
| 12 | H$_2$N— | Cpa- | DCys- | Aph(Cbm)- | DTrp- | Lys- | Thr- | Cys- | 2Nal- | NH$_2$ | 99 | 97 | 1219.45 | 1220.12 |
| 13 | Cbm- | Cpa- | DCys- | Aph(Cbm)- | DTrp- | Lys- | Thr- | Cys- | 2Nal- | NH$_2$ | 96 | 98 | 1262.46 | 1263.40 |
| 14 | DOTA- | Cpa- | DCys- | Aph(Cbm)- | DTrp- | Lys- | Thr- | Cys- | 2Nal- | NH$_2$ | 99 | 98 | 1605.64 | 1606.50 |
| 15 | DOTA-βAla- | Cpa- | DCys- | Aph(Cbm)- | DTrp- | Lys- | Thr- | Cys- | 2Nal- | NH$_2$ | 99 | 98 | 1676.67 | 1677.67 |
| 16 | DOTA-Peg- | Cpa- | DCys- | Aph(Cbm)- | DTrp- | Lys- | Thr- | Cys- | 2Nal- | NH$_2$ | 99 | 99 | 1809.62 | 1810.24 |
| 17 | H$_2$N— | Cpa- | DCys- | Aph(Cbm)- | DTrp- | Lys- | Thr- | Cys- | — | NH$_2$ | 99 | 99 | 1022.37 | 1023.49 |
| 18 | H$_2$N— | Cpa- | DCys- | Aph(Cbm)- | DTrp- | Lys- | Thr- | Cys- | Cha- | NH$_2$ | 99 | 96 | 1175.48 | 1176.36 |
| 19 | H$_2$N— | Cpa- | DCys- | Aph(Cbm)- | DTrp- | Lys- | Thr- | Cys- | Aph(Hor)- | NH$_2$ | 99 | 99 | 1324.47 | 1325.55 |
| 20 | H$_2$N— | Cpa- | DCys- | Aph(Cbm)- | DTrp- | Lys- | Thr- | Cys- | DAph(Cbm)- | NH$_2$ | 99 | 99 | 1227.45 | 1228.45 |
| 21 | H$_2$N— | Cpa- | DCys- | Aph(Cbm)- | DTrp- | Lys- | Thr- | Cys- | Aph(Cbm)- | NH$_2$ | 99 | 99 | 1227.45 | 1228.37 |
| 22 | H$_2$N— | Cpa- | DCys- | Aph(Cbm)- | DTrp- | Lys- | Thr- | Cys- | DAph(Cbm)- | Gly-OH | 98 | 98 | 1285.46 | 1286.34 |
| 23 | H$_2$N— | Cpa- | DCys- | Aph(CONH—OCH$_3$)— | DTrp- | Lys- | Thr- | Cys- | 2Nal- | NH$_2$ | 99 | 99 | 1249.46 | 1250.56 |
| 24 | H$_2$N— | Cpa- | DCys- | Aph(CONH—OH)— | DTrp- | Lys- | Thr- | Cys- | 2Nal- | NH$_2$ | 99 | 99 | 1235.44 | 1236.47 |
| 25 | H$_2$N— | Cpa- | DCys- | Aph(Cbm)- | 5F-DTrp- | Lys- | Thr- | Cys- | 2Nal- | NH$_2$ | 96 | 96 | 1237.44 | 1238.44 |
| 26 | H$_2$N— | Cpa- | DCys- | Aph(Cbm)- | 5F-Trp- | Lys- | Thr- | Cys- | 2Nal- | NH$_2$ | 96 | 85 | 1237.44 | 1238.24 |
| 27 | H$_2$N— | Cpa- | DCys- | Tyr- | DAph(Cbm)- | Lys- | Thr- | Cys- | 2Nal- | NH$_2$ | 99 | 99 | 1196.43 | 1197.36 |
| 28 | DOTA- | Cpa- | DCys- | Tyr- | DAph(Cbm)- | Lys- | Thr- | Cys- | 2Nal- | NH$_2$ | 99 | 99 | 1582.62 | 1583.72 |
| 29 | H$_2$N— | Cpa- | DCys- | Aph(Hor)- | DAph(Cbm)- | Lys- | Thr- | Cys- | 2Nal- | NH$_2$ | 91 | 95 | 1335.47 | 1336.44 |
| 30 | DOTA- | Cpa- | DCys- | Aph(Hor)- | DAph(Cbm)- | Lys- | Thr- | Cys- | 2Nal- | NH$_2$ | 95 | 94 | 1721.65 | 1722.56 |
| 31 | DOTA- | Cpa- | DCys- | Aph(Hor) | DAph(Cbm)- | Lys- | Thr- | Cys- | DTyr- | NH$_2$ | 96 | 97 | 1687.64 | 1688.83 |
| 32 | DOTA- | pNO$_2$Phe- | DCys- | ITyr- | DTrp- | Lys- | Thr- | Cys- | DTyr- | NH$_2$ | 99 | 99 | 1666.52 | 1667.74 |

[a]Percent purity determined by HPLC using buffer system: A = TEAP (pH 2.5) and B = 60% CH$_3$CN/40% A with a gradient slope of 1% B/min, at flow rate of 0.2 mL/min on a Vydac C$_{18}$ column (0.21 × 15 cm, 5-μm particle size, 300 Å pore size). Detection at 214 nm.
[b]Capillary zone electrophoresis (CZE) was done using a Beckman P/ACE System 2050 controlled by an IBM Personal System/2 Model 50Z and using a ChromJet integrator. Field strength of 15 kV at 30° C., mobile phase: 100 mM sodium phosphate (85:15, H$_2$O:CH$_3$CN) pH 2.50, on a Supelco P175 capillary (363 μm OD × 75 μm ID × 50 cm length). Detection at 214 nm.
[c]The calculated m/z of the monoisotope compared with the observed [M + H]$^+$ monoisotopic mass.

1. Bass, R. T., et al., *Identification and characterization of novel somatostatin antagonists*. Mol. Pharmacol., 1996. 50(4): p. 709-715.
2. Hocart, S. J., et al., *Highly potent cyclic disulfide antagonists of somatostatin*. J. Med. Chem., 1999. 42(11): p. 1863-1871.
3. Rajeswaran, W. G., et al., *Highly potent and subtype selective ligands derived by N-methyl scan of a somatostatin antagonist*. J. Med. Chem., 2001. 44(8): p. 1305-1311.

TABLE 3

Sst$_{1-5}$ Binding Affinities (IC$_{50}$s, nM) and Function of Sst$_2$-Selective Analogues.

| | sst1$^a$ | sst2$^a$ | sst3$^a$ | sst4$^a$ | sst5$^a$ | sst$_2$-internalization tested in vitro in HEK-sst$_2$ cells (n ≥ 2) | Calcium release tested in vitro in HEK-sst$_2$ cells (n ≥ 2) |
|---|---|---|---|---|---|---|---|
| SRIF-28 | 2.7 ± 0.2 | 2.7 ± 0.2 | 3.3 ± 0.4 | 2.6 ± 0.4 | 2.4 ± 0.2 | | |
| 1 | >1000 | 3.6 ± 0.4 | >1000 | 349 ± 30 | 276 ± 119 | Antagonist | |
| 2 | >1000 | 1.5 ± 0.4 | >1000 | 287 ± 27 | >1000 | Antagonist | Antagonist |
| 3 | >1000 | 0.75 ± 0.2 | >1000 | >1000 | >1000 | Antagonist | Antagonist |
| 4 | >1000 | 2.6 ± 0.7 | 384 ± 97 | >1000 | >1000 | Antagonist | |
| 5 | >1000 | 1.3 ± 0.2 | >1000 | >1000 | >1000 | Antagonist | Antagonist |
| 6 | >1000 | 2.7 ± 0.6 | 451 ± 80 | >1000 | >1000 | | |
| 7 | >1000 | 5.7 ± 1.5 | 112 ± 32 | 296 ± 19 | 218 ± 63 | Antagonist | Antagonist |
| 8 | >1000 | 10 ± 3.5 | 61 ± 14 | 715 ± 137 | 53 ± 19 | Antagonist | Antagonist |
| 9 | >1000 | 17 ± 5 | 827 ± 244 | >1000 | 442 ± 254 | Antagonist | |
| 10 | >1000 | 158 ± 37 | 102 ± 10 | 116 ± 47 | 728 ± 272 | | |
| 11 | >1000 | 58 ± 21 | 340 ± 77 | 908 ± 138 | 657 ± 299 | | |
| 12 | >1000 | 6.9 ± 0.7 | 155 ± 29 | 479 ± 8 | 149 ± 37 | Antagonist | Antagonist |
| 13 | >1000 | 23 ± 4.3 | 54 ± 15 | 136 ± 7.5 | 111 ± 17 | | |
| 14 | >1000 | 9.8 ± 1.2 | 972 ± 212 | 831 ± 82 | >1000 | Antagonist | Antagonist |
| 15 | >1000 | 46 ± 13 | 124 ± 53 | >1000 | >1000 | Antagonist | Antagonist |
| 16 | >1000 | 40 ± 1.5 | 88 ± 13 | 728 ± 158 | 895 ± 294 | Antagonist | |
| 17 | >1000 | 5.9 ± 1.8 | 138 ± 52 | >1000 | 461 ± 106 | Antagonist | Antagonist |
| 18 | >1000 | 4.1 ± 0.9 | 255 ± 79 | >1000 | 247 ± 66 | | |
| 19 | >1000 | 27 ± 3.8 | 162 ± 19 | >1000 | 320 ± 69 | | |
| 20 | >1000 | 5.4 ± 1 | 328 ± 69 | 800 ± 295 | 191 ± 49 | | |
| 21 | >1000 | 15 ± 3 | 336 ± 46 | 551 ± 151 | 560 ± 144 | | |
| 22 | >1000 | 52 ± 4.7 | 661 ± 115 | >1000 | 810 ± 200 | | |
| 23 | >1000 | 9.3 ± 0.9 | 157 ± 49 | 883 ± 174 | 313 ± 35 | | |
| 24 | >1000 | 9.3 ± 1.4 | 120 ± 45 | 813 ± 152 | 426 ± 189 | | |
| 25 | >1000 | 4.9 ± 1.5 | 50 ± 5.8 | 287 ± 64 | 94 ± 34 | Antagonist | Antagonist |
| 26 | >1000 | 23 ± 3.7 | 90 ± 11 | 905 ± 132 | 618 ± 248 | | |
| 27 | >1000 | 3.7 ± 1.3 | 346 ± 81 | >1000 | >1000 | | |
| 28 | >1000 | 1.4 ± 0.5 | >1000 | >1000 | >1000 | Antagonist | Antagonist |
| 29 | >1000 | 2.4 ± 0.6 | 83 ± 2.0 | >1000 | >1000 | Antagonist | Antagonist |
| 30 | >1000 | 1.7 ± 0.2 | >1000 | >1000 | >1000 | Antagonist | Antagonist |
| 31 | >1000 | 0.7 ± 0.12 | >1000 | >1000 | >1000 | Antagonist | Antagonist |
| 32 | >1000 | 1.2 ± 0.4 | >1000 | 455 ± 125 | >1000 | Antagonist | Antagonist |

$^a$The IC$_{50}$ values (nM) were derived from competitive radioligand displacement assays reflecting the affinities of the analogues for the cloned SRIF receptors using the non-selective [Leu$^8$,DTrp$^{22}$,$^{125}$I-Tyr$^{25}$]SRIF-28, as the radioligand. Mean value ± SEM when N ≥ 3.

What is claimed is:

1. A somatostatin antagonist that binds to SSTR2; is not significantly internalized into cells expressing SSTR2, and reduces octreotide-induced internalization of SSTR2, wherein the antagonist is a cyclic somatostatin (SRIF) peptide antagonist comprising the amino acid sequence (cyclo 3-14) Xaa$_1$-Xaa$_2$-D-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$;

Xaa$_1$ is des-Xaa;

Xaa$_2$ is Trp(A), Phe(B), Nal or Tyr, wherein A is H, Cl, F, Br, Me, NO$_2$, OMe or N-formyl and B is H, halogen, CH$_3$, NO$_2$ or OCH$_3$;

D-Xaa$_3$ is D-Cys, D-Pen, D-HCys or another D-isomer α-amino acid having an SH-side chain;

Xaa$_4$, Xaa$_5$ and Xaa$_6$ are des-Xaa;

Xaa$_7$ is Aph(Q$_1$), Tyr, ITyr, Ala(thienyl) or Trp(A) where Q$_1$ is Cbm, OH—Cbm, CH$_3$-Cbm, OCH$_3$-Cbm, OEt-Cbm, Cbm-Et(OEt)$_2$ or Hor;

Xaa$_8$ is D-Trp(A), Trp(A), Tyr, D-Tyr, Phe(B), D-Phe(B), L or D-BzlHis, L or D-(DNP)His, L or D-Aph(Cbm);

Xaa$_9$ is Lys, N$^\alpha$MeLys, hLys, N$^\alpha$MehLys, Orn or N$^\alpha$Me-Orn;

Xaa$_{10}$ is Thr, Ser or Val;

Xaa$_{11}$, Xaa$_{12}$ and Xaa$_{13}$ are des-Xaa;

Xaa$_{14}$ is Cys, Pen, hCys or another L-isomer α-amino acid having an SH side chain;

Xaa$_{15}$ is 2Nal, D-2Nal, Aph(Q$_2$), D-Aph(Q$_2$), (R$_1$)Cha, (R$_1$)D-Cha, (R$_1$)Leu, (R$_1$)D-Leu, Tyr, D-Tyr, Trp, D-Trp or des-Xaa; wherein R$_1$ is H or C$^\alpha$Me, and Q$_2$ is Cbm, OH-Cbm, CH$_3$-Cbm, OCH$_3$-Cbm or OEt-Cbm; and Xaa$_{15}$ is optionally amidated or is C-terminated with Gly-OH group.

2. The somatostatin antagonist of claim 1, wherein the antagonist is selected from the group consisting of:
(i) DOTA-pNO$_2$Phe-c[DCys-Tyr-DTrp-Lys-Thr-Cys]-DTyr-NH$_2$;
(ii) DOTA-pNO$_2$Phe-c[DCys-Tyr-DAph(Cbm)-Lys-Thr-Cys]-DTyr-NH$_2$;
(iii) H$_2$N-pNO$_2$Phe-c[DCys-Tyr-DAph(Cbm)-Lys-Thr-Cys]-2Nal-NH$_2$;
(iv) DOTA-pNO$_2$Phe-c[DCys-Tyr-DAph(Cbm)-Lys-Thr-Cys]-2Nal-NH$_2$;
(v) H$_2$N-pNO$_2$Phe-c[DCys-Aph(Hor)-DAph(Cbm)-Lys-Thr-Cys]-2Nal-NH$_2$;
(vi) H$_2$N-Cpa-c[DCys-L-Agl(NMe.benzoyl)-DTrp-Lys-Thr-Cys]-2Nal-NH$_2$;
(vii) H$_2$N-Cpa-c[DCys-D-Agl(NMe.benzoyl)-DTrp-Lys-Thr-Cys]-2Nal-NH$_2$;
(viii) H$_2$N-Cpa-c[DCys-Leu-DTrp-Lys-Thr-Cys]-2Nal-NH$_2$;
(ix) H$_2$N-Cpa-c[DCys-Aph(Cbm)-DTrp-Lys-Thr-Cys]-2Nal-NH$_2$;
(x) Cbm-Cpa-c[DCys-Aph(Cbm)-DTrp-Lys-Thr-Cys]-2Nal-NH$_2$;

(xi) DOTA-Cpa-c[DCys-Aph(Cbm)-DTrp-Lys-Thr-Cys]-2Nal-NH$_2$;
(xii) DOTA-bAla-Cpa-c[DCys-Aph(Cbm)-DTrp-Lys-Thr-Cys]-2Nal-NH$_2$;
(xiii) DOTA-Peg-Cpa-c[DCys-Aph(Cbm)-DTrp-Lys-Thr-Cys]-2Nal-NH$_2$;
(xiv) H$_2$N-Cpa-c[DCys-Aph(Cbm)-DTrp-Lys-Thr-Cys]-NH$_2$;
(xv) H$_2$N-Cpa-c[DCys-Aph(Cbm)-DTrp-Lys-Thr-Cys]-Cha-NH$_2$;
(xvi) H$_2$N-Cpa-c[DCys-Aph(Cbm)-DTrp-Lys-Thr-Cys]-Aph(Hor)-NH$_2$;
(xvii) H$_2$N-Cpa-c[DCys-Aph(Cbm)-DTrp-Lys-Thr-Cys]-DAph(Cbm)-NH$_2$;
(xviii) H$_2$N-Cpa-c[DCys-Aph(Cbm)-DTrp-Lys-Thr-Cys]-Aph(Cbm)-NH$_2$;
(xix) H$_2$N-Cpa-c[DCys-Aph(Cbm)-DTrp-Lys-Thr-Cys]-DAph(Cbm)-GlyOH;
(xx) H$_2$N-Cpa-c[DCys-Aph(CONH—OCH$_3$)-DTrp-Lys-Thr-Cys]-2Nal-NH$_2$;
(xxi) H$_2$N-Cpa-c[DCys-Aph(CONH—OH)-DTrp-Lys-Thr-Cys]-2Nal-NH$_2$;
(xxii) H$_2$N-Cpa-c[DCys-Aph(Cbm)-5F-DTrp-Lys-Thr-Cys]-2Nal-NH$_2$;
(xxiii) H$_2$N-Cpa-c[DCys-Aph(Cbm)-5F-Trp-Lys-Thr-Cys]-2Nal-NH$_2$;
(xxiv) H$_2$N-Cpa-c[DCys-Tyr-DAph(Cbm)-Lys-Thr-Cys]-2Nal-NH$_2$;
(xxv) DOTA-Cpa-c[DCys-Tyr-DAph(Cbm)-Lys-Thr-Cys]-2Nal-NH$_2$;
(xxvi) H$_2$N-Cpa-c[DCys-Aph(Hor)-DAph(Cbm)-Lys-Thr-Cys]-2Nal-NH$_2$;
(xxvii) DOTA-Cpa-c[DCys-Aph(Hor)-DAph(Cbm)-Lys-Thr-Cys]-2Nal-NH$_2$;
(xxviii) DOTA-Cpa-c[DCys-Aph(Hor)-DAph(Cbm)-Lys-Thr-Cys]-DTyr-NH$_2$; and
(xxix) DOTA-pNO$_2$Phe-c[DCys-ITyr-DTrp-Lys-Thr-Cys]-DTyr-NH$_2$.

3. The somatostatin antagonist of claim 1, further comprising a chelator, a complexing agent, a conjugating agent or a label.

4. A pharmaceutical composition comprising the somatostatin antagonist of claim 1 and at least one pharmaceutically acceptable excipient.

5. A kit for the diagnostic radioimaging of cancer, wherein the cells of said cancer have functional somatostatin receptors, comprising:
(a) a somatostatin antagonist in a suitable container, wherein the somatostatin antagonist is either:
 (i) labeled with at least one radionuclide;
 (ii) unlabeled and provided with at least one radionuclide in a suitable container for labeling; or
 (iii) unlabeled and capable of being subsequently labeled with at least one radionuclide; and
(b) instructions for use: and wherein;
 the somatostatin antagonist selectively binds to SSTR2: cells of said cancer have functional SSTR2 receptors; and
 the somatostatin antagonist is a cyclic somatostatin peptide antagonist comprising the amino acid sequence (cyclo 3-14) Xaa$_1$-Xaa$_2$-D-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$,
Xaa$_1$ is des-Xaa;
Xaa$_2$ is Trp(A), Phe(B), Nal or Tyr, wherein A is H, Cl, F, Br, Me, NO$_2$, OMe or N-formyl and B is H, halogen, CH$_3$, NO$_2$ or OCH$_3$;
D-Xaa$_3$ is D-Cys, D-Pen, D-HCys or another D-isomer α-amino acid having an SH-side chain;
Xaa$_4$, Xaa$_5$ and Xaa$_6$ are des-Xaa;
Xaa$_7$ is Aph(Q$_1$), Tyr, ITyr, Ala(thienyl) or Trp(A) where Q$_1$ is Cbm, OH-Cbm, CH$_3$-Cbm, OCH$_3$-Cbm, OEt-Cbm, Cbm-Et(OEt)$_2$ or Hor;
Xaa$_8$ is D-Trp(A), Trp(A), Tyr, D-Tyr, Phe(B), D-Phe (B), L or D-BzlHis, L or D-(DNP)His, L or D-Aph (Cbm);
Xaa$_9$ is Lys, N$^\alpha$MeLys, hLys, N$^\alpha$MehLys, Orn or N$^\alpha$Me-Orn;
Xaa$_{10}$ is Thr, Ser or Val;
Xaa$_{11}$, Xaa$_{12}$ and Xaa$_{13}$ are des-Xaa;
Xaa$_{14}$ is Cys, Pen, hCys or another L-isomer α-amino acid having an SH side chain;
Xaa$_{15}$ is 2Nal, D-2Nal, Aph(Q$_2$), D-Aph(Q$_2$), (R$_1$)Cha, (R$_1$)D-Cha, (R$_1$)Leu, (R$_1$)D-Leu, Tyr, D-Tyr, Trp, D-Trp or des-Xaa; wherein R$_1$ is H or C$^\alpha$Me, and Q$_2$ is Cbm, OH-Cbm, CH$_3$-Cbm, OCH$_3$-Cbm or OEt-Cbm; and Xaa$_{15}$ is optionally amidated or is C-terminated with Gly-OH group.

6. The kit of claim 5, wherein the peptide is selected from the group consisting of:
(i) Ac-pNO$_2$Phe-c[DCys-Tyr-DTrp-Lys-Thr-Cys]-DTyr-NH$_2$;
(ii) DOTA-pNO$_2$Phe-c[DCys-Tyr-DTrp-Lys-Thr-Cys]-DTyr-NH$_2$;
(iii) DOTA-pNO$_2$Phe-c[DCys-Tyr-DAph(Cbm)-Lys-Thr-Cys]-DTyr-NH$_2$;
(iv) H$_2$N-pNO$_2$Phe-c[DCys-Tyr-DAph(Cbm)-Lys-Thr-Cys]-2Nal-NH$_2$;
(v) DOTA-pNO$_2$Phe-c[DCys-Tyr-DAph(Cbm)-Lys-Thr-Cys]-2Nal-NH$_2$;
(vi) H$_2$N-pNO$_2$Phe-c[DCys-Aph(Hor)-DAph(Cbm)-Lys-Thr-Cys]-2Nal-NH$_2$;
(vii) H$_2$N-Cpa-c[DCys-Tyr-DTrp-Lys-Thr-Cys]-2Nal-NH$_2$;
(viii) H$_2$N-Cpa-c[DCys-Tyr-DTrp-NMeLys-Thr-Cys]-2Nal-NH$_2$;
(ix) H$_2$N-Cpa-c[DCys-L-Agl(NMe.benzoyl)-DTrp-Lys-Thr-Cys]-2Nal-NH$_2$;
(x) H$_2$N-Cpa-c[DCys-D-Agl(NMe.benzoyl)-DTrp-Lys-Thr-Cys]-2Nal-NH$_2$;
(xi) H$_2$N-Cpa-c[DCys-Leu-DTrp-Lys-Thr-Cys]-2Nal-NH$_2$;
(xii) H$_2$N-Cpa-c[DCys-Aph(Cbm)-DTrp-Lys-Thr-Cys]-2Nal-NH$_2$;
(xiii) Cbm-Cpa-c[DCys-Aph(Cbm)-DTrp-Lys-Thr-Cys]-2Nal-NH$_2$;
(xiv) DOTA-Cpa-c [DCys-Aph(Cbm)-DTrp-Lys-Thr-Cys]-2Nal-NH$_2$;
(xv) DOTA-bAla-Cpa-c[DCys-Aph(Cbm)-DTrp-Lys-Thr-Cys]-2Nal-NH$_2$;
(xvi) DOTA-Peg-Cpa-c [DCys-Aph(Cbm)-DTrp-Lys-Thr-Cys]-2Nal-NH$_2$;
(xvii) H$_2$N-Cpa-c[DCys-Aph(Cbm)-DTrp-Lys-Thr-Cys]-NH$_2$;
(xviii) H$_2$N-Cpa-c[DCys-Aph(Cbm)-DTrp-Lys-Thr-Cys]-Cha-NH$_2$;
(xix) H$_2$N-Cpa-c[DCys-Aph(Cbm)-DTrp-Lys-Thr-Cys]-Aph(Hor)-NH$_2$;
(xx) H$_2$N-Cpa-c[DCys-Aph(Cbm)-DTrp-Lys-Thr-Cys]-DAph(Cbm)-NH$_2$;
(xxi) H$_2$N-Cpa-c[DCys-Aph(Cbm)-DTrp-Lys-Thr-Cys]-Aph(Cbm)-NH$_2$;
(xxii) H$_2$N-Cpa-c[DCys-Aph(Cbm)-DTrp-Lys-Thr-Cys]-DAph(Cbm)-GlyOH;

(xxiii) H₂N-Cpa-c[DCys-Aph(CONH-OCH₃)-DTrp-Lys-Thr-Cys]-2Nal-NH₂;
(xxiv) H₂N-Cpa-c[DCys-Aph(CONH-OH)-DTrp-Thr-Cys]-2Nal-NH₂;
(xxv) H₂N-Cpa-c[DCys-Aph(Cbm)-5F-DTrp-Lys-Thr-Cys]-2Nal-NH₂;
(xxvi) H₂N-Cpa-c[DCys-Aph(Cbm)-5F-Trp-Lys-Thr-Cys]-2Nal-NH₂;
(xxvii) H₂N-Cpa-c[DCys-Tyr-DAph(Cbm)-Lys-Thr-Cys]-2Nal-NH₂;
(xxviii) DOTA-Cpa-c[DCys-Tyr-DAph(Cbm)-Lys-Thr-Cys]-2Nal-NH₂;
(xxix) H₂N-Cpa-c[DCys-Aph(Hor)-DAph(Cbm)-Lys-Thr-Cys]-2Nal-NH₂;
(xxx) DOTA-Cpa-c[DCys-Aph(Hor)-DAph(Cbm)-Lys-Thr-Cys]-2Nal-NH₂;
(xxxi) DOTA-Cpa-c[DCys-Aph(Hor)-DAph(Cbm)-Lys-Thr-Cys]-DTyr-NH₂; and
(xxxii) DOTA-pNO₂Phe-c[DCys-ITyr-DTrp-Lys-Thr-Cys]-DTyr-NH₂.

7. A kit for the treatment of cancer, wherein the cells of said cancer have functional somatostatin receptors, comprising
(a) a somatostatin antagonist in a suitable container, wherein, upon radionuclide labeling of the somatostatin antagonist, the antagonist is present in a therapeutically effective amount for cancer treatment, and wherein the somatostatin antagonist is either:
  (i) labeled with at least one radionuclide,
  (ii) unlabeled, and provided with at least one radionuclide in a suitable container for labeling, or
  (iii) unlabeled, and capable of being subsequently labeled with at least one radionuclide; and
(b) instructions for use; and
wherein:
  the somatostatin antagonist selectively binds to SSTR2:
  cells of said cancer have functional SSTR2 receptors; and
  the somatostatin antagonist is a cyclic somatostatin peptide antagonist comprising the amino acid sequence (cyclo 3-14) $Xaa_1$-$Xaa_2$-D-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$,
  $Xaa_1$ is des-Xaa;
  $Xaa_2$ is Trp(A), Phe(B), Nal or Tyr, wherein A is H, Cl, F, Br, Me, NO₂, OMe or N-formyl and B is H, halogen, CH₃, NO₂ or OCH₃;
  D-$Xaa_3$ is D-Cys, D-Pen, D-HCys or another D-isomer α-amino acid having an SH-side chain;
  $Xaa_4$, $Xaa_5$ and $Xaa_6$ are des-Xaa;
  $Xaa_7$ is Aph($Q_1$), Tyr, ITyr, Ala(thienyl) or Trp(A) where $Q_1$ is Cbm, OH-Cbm, CH₃-Cbm, OCH₃-Cbm, OEt-Cbm, Cbm-Et(OEt)₂ or Hor;
  $Xaa_8$ is D-Trp(A), Trp(A), Tyr, D-Tyr, Phe(B), D-Phe(B), L or D-zlHis, L or D-(DNP)His, L or D-Aph(Cbm);
  $Xaa_9$ is Lys, $N^\alpha$MeLys, hLys, $N^\alpha$MehLys, Orn or $N^\alpha$Me-Orn;
  $Xaa_{10}$ is Thr, Ser or Val;
  $Xaa_{11}$, $Xaa_{12}$ and $Xaa_{13}$ are des-Xaa;
  $Xaa_{14}$ is Cys, Pen, hCys or another L-isomer α-amino acid having an SH side chain;
  $Xaa_{15}$ is 2Nal, D-2Nal, Aph($Q_2$), D-Aph($Q_2$), ($R_1$)Cha, ($R_1$)D-Cha, ($R_1$)Leu, ($R_1$)D-Leu, Tyr, D-Tyr, Trp, D-Trp or des-Xaa; wherein $R_1$ is H or $C^\alpha$Me, and $Q_2$ is Cbm, OH-Cbm, CH₃-Cbm, OCH₃-Cbm or OEt-Cbm; and $Xaa_{15}$ is optionally amidated or is C-terminated with Gly-OH group.

8. The kit of claim 7, wherein the peptide is selected from the group consisting of:
(i) Ac-pNO₂Phe-c[DCys-Tyr-DTrp-Lys-Thr-Cys]-DTyr-NH₂;
(ii) DOTA-pNO₂Phe-c[DCys-Tyr-DTrp-Lys-Thr-Cys]-DTyr-NH₂;
(iii) DOTA-pNO₂Phe-c[DCys-Tyr-D Aph(Cbm)-Lys-Thr-Cys]-DTyr-NH₂;
(iv) H₂N-pNO₂Phe-c[DCys-Tyr-D Aph(Cbm)-Lys-Thr-Cys]-2Nal-NH₂;
(v) DOTA-pNO₂Phe-c[DCys-Tyr-D Aph(Cbm)-Lys-Thr-Cys]-2Nal-NH₂;
(vi) H₂N-pNO₂Phe-c[DCys-Aph(Hor)-DAph(Cbm)-Lys-Thr-Cys]-2Nal-NH₂;
(vii) H₂N-Cpa-c[DCys-Tyr-DTrp-Lys-Thr-Cys]-2Nal-NH₂;
(viii) H₂N-Cpa-c[DCys-Tyr-DTrp-NMeLys-Thr-Cys]-2Nal-NH₂;
(ix) H₂N-Cpa-c[DCys-L-Agl(NMe.benzoyl)-DTrp-Lys-Thr-Cys]-2Nal-NH₂;
(x) H₂N-Cpa-c[DCys-D-Agl(NMe.benzoyl)-DTrp-Lys-Thr-Cys]-2Nal-NH₂;
(xi) H₂N-Cpa-c[DCys-Leu-DTrp-Lys-Thr-Cys]-2Nal-NH₂;
(xii) H₂N-Cpa-c[DCys-Aph(Cbm)-DTrp-Lys-Thr-Cys]-2Nal-NH₂;
(xiii) Cbm-Cpa-c[DCys-Aph(Cbm)-DTrp-Lys-Thr-Cys]-2Nal-NH₂;
(xiv) DOTA-Cpa-c[DCys-Aph(Cbm)-DTrp-Lys-Thr-Cys]-2Nal-NH₂;
(xv) DOTA-bAla-Cpa-c[DCys-Aph(Cbm)-DTrp-Lys-Thr-Cys]-2Nal-NH₂;
(xvi) DOTA-Peg-Cpa-c[DCys-Aph(Cbm)-DTrp-Lys-Thr-Cys]-2Nal-NH₂;
(xvii) H₂N-Cpa-c[DCys-Aph(Cbm)-DTrp-Lys-Thr-Cys]-NH₂;
(xviii) H₂N-Cpa-c[DCys-Aph(Cbm)-DTrp-Lys-Thr-Cys]-Cha-NH₂;
(xix) H₂N-Cpa-c[DCys-Aph(Cbm)-DTrp-Lys-Thr-Cys]-Aph(Hor)-NH₂;
(xx) H₂N-Cpa-c[DCys-Aph(Cbm)-DTrp-Lys-Thr-Cys]-DAph(Cbm)-NH₂;
(xxi) H₂N-Cpa-c[DCys-Aph(Cbm)-DTrp-Lys-Thr-Cys]-Aph(Cbm)-NH₂;
(xxii) H₂N-Cpa-c[DCys-Aph(Cbm)-DTrp-Lys-Thr-Cys]-DAph(Cbm)-GlyOH;
(xxiii) H₂N-Cpa-c[DCys-Aph(CONH—OCH₃)-DTrp-Lys-Thr-Cys]-2Nal-NH₂;
(xxiv) H₂N-Cpa-c[DCys-Aph(CONH—OH)-DTrp-Lys-Thr-Cys]-2Nal-NH₂;
(xxv) H₂N-Cpa-c[DCys-Aph(Cbm)-5F-DTrp-Lys-Thr-Cys]-2Nal-NH₂;
(xxvi) H₂N-Cpa-c[DCys-Aph(Cbm)-5F-Trp-Lys-Thr-Cys]-2Nal-NH₂;
(xxvii) H₂N-Cpa-c[DCys-Tyr-DAph(Cbm)-Lys-Thr-Cys]-2Nal-NH₂;
(xxviii) DOTA-Cpa-c[DCys-Tyr-DAph(Cbm)-Lys-Thr-Cys]-2Nal-NH₂;
(xxix) H₂N-Cpa-c[DCys-Aph(Hor)-DAph(Cbm)-Lys-Thr-Cys]-2Nal-NH₂;
(xxx) DOTA-Cpa-c[DCys-Aph(Hor)-DAph(Cbm)-Lys-Thr-Cys]-2Nal-NH₂;
(xxxi) DOTA-Cpa-c[DCys-Aph(Hor)-DAph(Cbm)-Lys-Thr-Cys]-DTyr-NH₂; and
(xxxii) DOTA-pNO₂Phe-c[DCys-ITyr-DTrp-Lys-Thr-Cys]-DTyr-NH₂.

9. A composition for radioimaging or treating tumor cells comprising an effective amount of a radionuclide coupled to a somatostatin antagonist; wherein the antagonist selectively binds to SSTR2, is not significantly internalized into cells expressing SSTR2;

the antagonist reduces octreotide-induced internalization of SSTR2; and wherein cells of said cancer have functional SSTR2 receptors;

the antagonist is a cyclic somatostatin (SRIF) peptide antagonist comprising the amino acid sequence (cyclo 3-14) $Xaa_1$-$Xaa_2$-D-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$, $Xaa_1$ is des-Xaa;

$Xaa_2$ is Trp(A), Phe(B), Nal or Tyr, wherein A is H, Cl, F, Br, Me, $NO_2$, OMe or N-formyl and B is H, halogen, $CH_3$, $NO_2$ or $OCH_3$;

D-$Xaa_3$ is D-Cys, D-Pen, D-HCys or another D-isomer α-amino acid having an SH-side chain;

$Xaa_4$, $Xaa_5$ and $Xaa_6$ are des-Xaa;

$Xaa_7$ is Aph($Q_1$), Tyr, ITyr, Ala(thienyl) or Trp(A) where $Q_1$ is Cbm, OH-Cbm, $CH_3$-Cbm, $OCH_3$-Cbm, OEt-Cbm, Cbm-Et(OEt)$_2$ or Hor;

$Xaa_8$ is D-Trp(A), Trp(A), Tyr, D-Tyr, Phe(B), D-Phe(B), L or D-BzlHis, L or D-(DNP)His, L or D-Aph(Cbm);

$Xaa_9$ is Lys, $N^\alpha$MeLys, hLys, $N^\alpha$MehLys, Orn or $N^\alpha$Me-Orn;

$Xaa_{10}$ is Thr, Ser or Val;

$Xaa_{11}$, $Xaa_{12}$ and $Xaa_{13}$ are des-Xaa;

$Xaa_{14}$ is Cys, Pen, hCys or another L-isomer α-amino acid having an SH side chain;

$Xaa_{15}$ is 2Nal, D-2Nal, Aph($Q_2$), D-Aph($Q_2$), ($R_1$)Cha, ($R_1$)D-Cha, ($R_1$)Leu, ($R_1$)D-Leu, Tyr, D-Tyr, Trp, D-Trp or des-Xaa; wherein $R_1$ is H or $C^\alpha$Me, and $Q_2$ is Cbm, OH-Cbm, $CH_3$-Cbm, $OCH_3$-Cbm or OEt-Cbm; and $Xaa_{15}$ is optionally amidated or is C-terminated with Gly-OH group.

10. A compound for radioimaging or treating tumor cells comprising an effective amount of a radionuclide coupled to a somatostatin antagonist; wherein said antagonist binds to SSTR2and is selected from the group consisting of:

(i) DOTA-pNO$_2$Phe-c[DCys-Tyr-DTrp-Lys-Thr-Cys]-DTyr-NH$_2$;

(iii) DOTA-pNO$_2$Phe-c[DCys-Tyr-D Aph(Cbm)-Lys-Thr-Cys]-DTyr-NH$_2$;

(iii) H$_2$N-pNO$_2$Phe-c[DCys-Tyr-DAph(Cbm)-Lys-Thr-Cys]-2Nal-NH$_2$;

(iv) DOTA-pNO$_2$Phe-c[DCys-Tyr-DAph(Cbm)-Lys-Thr-Cys]-2Nal-NH$_2$;

(v) H$_2$N-pNO$_2$Phe-c[DCys-Aph(Hor)-DAph(Cbm)-Lys-Thr-Cys]-2Nal-NH$_2$;

(vi) H$_2$N-Cpa-c[DCys-L-Agl(NMe.benzoyl)-DTrp-Lys-Thr-Cys]-2Nal-NH$_2$;

(vii) H$_2$N-Cpa-c[DCys-D-Agl(NMe.benzoyl)-DTrp-Lys-Thr-Cys]-2Nal-NH$_2$;

(viii) H$_2$N-Cpa-c[DCys-Leu-DTrp-Lys-Thr-Cys]-2Nal-NH$_2$;

(ix) H$_2$N-Cpa-c[DCys-Aph(Cbm)-DTrp-Lys-Thr-Cys]-2Nal-NH$_2$;

(x) Cbm-Cpa-c[DCys-Aph(Cbm)-DTrp-Lys-Thr-Cys]-2Nal-NH$_2$;

(xi) DOTA-Cpa-c[DCys-Aph(Cbm)-DTrp-Lys-Thr-Cys]-2Nal-NH$_2$;

(xii) DOTA-bAla-Cpa-c[DCys-Aph(Cbm)-DTrp-Lys-Thr-Cys]-2Nal-NH$_2$;

(xiii) DOTA-Peg-Cpa-c[DCys-Aph(Cbm)-DTrp-Lys-Thr-Cys]-2Nal-NH$_2$;

(xiv) H$_2$N-Cpa-c[DCys-Aph(Cbm)-DTrp-Lys-Thr-Cys]-NH$_2$;

(xv) H$_2$N-Cpa-c[DCys-Aph(Cbm)-DTrp-Lys-Thr-Cys]-Cha-NH$_2$;

(xvi) H$_2$N-Cpa-c[DCys-Aph(Cbm)-DTrp-Lys-Thr-Cys]-Aph(Hor)-NH$_2$;

(xvii) H$_2$N-Cpa-c[DCys-Aph(Cbm)-DTrp-Lys-Thr-Cys]-DAph(Cbm)-NH$_2$;

(xviii) H$_2$N-Cpa-c[DCys-Aph(Cbm)-DTrp-Lys-Thr-Cys]-Aph(Cbm)-NH$_2$;

(xix) H$_2$N-Cpa-c[DCys-Aph(Cbm)-DTrp-Lys-Thr-Cys]-DAph(Cbm)-GlyOH;

(xx) H$_2$N-Cpa-c[DCys-Aph(CONH—OCH$_3$)-DTrp-Lys-Thr-Cys]-2Nal-NH$_2$;

(xxi) H$_2$N-Cpa-c[DCys-Aph(CONH—OH)-DTrp-Lys-Thr-Cys]-2Nal-NH$_2$;

(xxii) H$_2$N-Cpa-c[DCys-Aph(Cbm)-5F-DTrp-Lys-Thr-Cys]-2Nal-NH$_2$;

(xxiii) H$_2$N-Cpa-c[DCys-Aph(Cbm)-5F-Trp-Lys-Thr-Cys]-2Nal-NH$_2$;

(xxiv) H$_2$N-Cpa-c[DCys-Tyr-DAph(Cbm)-Lys-Thr-Cys]-2Nal-NH$_2$;

(xxv) DOTA-Cpa-c[DCys-Tyr-DAph(Cbm)-Lys-Thr-Cys]-2Nal-NH$_2$;

(xxvi) H$_2$N-Cpa-c[DCys-Aph(Hor)-DAph(Cbm)-Lys-Thr-Cys]-2Nal-NH$_2$;

(xxvii) DOTA-Cpa-c[DCys-Aph(Hor)-DAph(Cbm)-Lys-Thr-Cys]-2Nal-NH$_2$;

(xxviii) DOTA-Cpa-c[DCys-Aph(Hor)-DAph(Cbm)-Lys-Thr-Cys]-DTyr-NH$_2$; and (xxix) DOTA-pNO$_2$Phe-c[DCys-ITyr-DTrp-Lys-Thr-Cys]-DTyr-NH$_2$.

* * * * *